(12) United States Patent
Fernandes et al.

(10) Patent No.: US 11,642,490 B2
(45) Date of Patent: May 9, 2023

(54) PATCH SYSTEM FOR MONITORING AND ENHANCING SLEEP AND CIRCADIAN RHYTHM ALIGNMENT

(71) Applicant: Circadian Positioning Systems, Inc., Newport, RI (US)

(72) Inventors: Gustavo E. Fernandes, Providence, RI (US); Eliza Van Reen, East Greenwich, RI (US)

(73) Assignee: Circadian Positioning Systems, Inc., Newport, RI (US)

( * ) Notice: Subject to any disclaimer, the term of this patent is extended or adjusted under 35 U.S.C. 154(b) by 1094 days.

(21) Appl. No.: 16/258,472

(22) Filed: Jan. 25, 2019

(65) Prior Publication Data

US 2019/0224445 A1    Jul. 25, 2019

Related U.S. Application Data

(60) Provisional application No. 62/692,292, filed on Jun. 29, 2018, provisional application No. 62/621,898, filed on Jan. 25, 2018.

(51) Int. Cl.
  *A61M 21/02* (2006.01)
  *A61B 5/01* (2006.01)
  (Continued)

(52) U.S. Cl.
  CPC ............... *A61M 21/02* (2013.01); *A61B 5/01* (2013.01); *A61B 5/163* (2017.08); *A61B 5/4809* (2013.01);
  (Continued)

(58) Field of Classification Search
  CPC .................. A61M 21/00; A61M 21/02; A61M 2021/0005; A61M 2021/0011;
  (Continued)

(56) References Cited

U.S. PATENT DOCUMENTS

| 5,508,039 | A  | 4/1996  | Yates et al.    |
| 10,850,061 | B2 | 12/2020 | Van Reen et al. |

(Continued)

FOREIGN PATENT DOCUMENTS

| WO | WO 2013/184965 A1 | 12/2013 |
| WO | WO 2017/214630 A1 | 12/2017 |
| WO | WO 2018/218241 A1 | 11/2018 |

OTHER PUBLICATIONS

International Search Report issued in International Application No. PCT/US2019/015292, dated Jun. 6, 2019.

*Primary Examiner* — Carrie R Dorna
(74) *Attorney, Agent, or Firm* — Morse, Barnes-Brown & Pendleton, P.C.; Stanley F. Chalvire, Esq.

(57) ABSTRACT

Disclosed are novel compositions, devices, patches, systems and methods that are useful for estimating, determining, modulating and/or improving the sleep/wake and/or circadian phase of a subject (e.g., a human subject) by the dispensing of measured quantities of agents to a subject or into an environment of the subject and the continuous monitoring and/or tracking of the subject's consciousness (e.g., sleep/wake) patterns. In certain aspects, the compositions, devices, patches, systems and methods disclosed herein are capable of delivering one or more agents to a subject in response to measured consciousness patterns estimations and circadian phase estimations, thereby aligning the subject's circadian biology to the external environment and improving the quality and duration of sleep.

11 Claims, 16 Drawing Sheets

(51) Int. Cl.
  *A61B 5/145* (2006.01)
  *A61B 5/00* (2006.01)
  *A61B 5/16* (2006.01)
  *A61M 21/00* (2006.01)
  *A61K 9/70* (2006.01)
  *A61B 5/1455* (2006.01)
  *A61B 5/0205* (2006.01)
  *A61B 5/291* (2021.01)
  *A61B 5/398* (2021.01)

(52) U.S. Cl.
  CPC .......... *A61B 5/4815* (2013.01); *A61B 5/6833* (2013.01); *A61B 5/02055* (2013.01); *A61B 5/1455* (2013.01); *A61B 5/14517* (2013.01); *A61B 5/291* (2021.01); *A61B 5/398* (2021.01); *A61B 5/4821* (2013.01); *A61B 5/4839* (2013.01); *A61B 2562/0219* (2013.01); *A61K 9/7023* (2013.01); *A61M 2021/0005* (2013.01)

(58) Field of Classification Search
  CPC .. A61M 2021/0016; A61M 2021/0077; A61M 2021/0083; A61N 5/01; A61N 5/4815; A61N 5/14517; A61N 5/1455; A61N 5/4821; A61N 5/4839; A61N 5/4809
  See application file for complete search history.

(56) References Cited

U.S. PATENT DOCUMENTS

| | | |
|---|---|---|
| 2002/0028991 A1 | 3/2002 | Thompson |
| 2004/0097871 A1 | 5/2004 | Yerushalmy |
| 2005/0113646 A1 | 5/2005 | Sotos et al. |
| 2008/0262376 A1 | 10/2008 | Price |
| 2009/0259176 A1 | 10/2009 | Yairi |
| 2009/0326616 A1 | 12/2009 | Aarts et al. |
| 2010/0143448 A1 | 6/2010 | Nisato et al. |
| 2014/0207047 A1 | 7/2014 | DiPierro |
| 2014/0276552 A1 | 9/2014 | Nguyen |
| 2014/0288385 A1 | 9/2014 | Amurthur |
| 2015/0087894 A1 | 3/2015 | Rink et al. |
| 2017/0014572 A1 | 1/2017 | Newberry |
| 2017/0181699 A1* | 6/2017 | Pronk ................. A61B 5/7275 |
| 2021/0023333 A1 | 1/2021 | Van Reen et al. |

\* cited by examiner

PATCH SYSTEM FOR MONITORING AND ENHANCING SLEEP AND CIRCADIAN RHYTHM ALIGNMENT

CROSS-REFERENCE TO RELATED APPLICATION(S)

This application claims priority to, and the benefit of, co-pending U.S. Provisional Application No. 62/621,898, filed Jan. 25, 2018, and co-pending U.S. Provisional Application No. 62/692,292, filed Jun. 29, 2018. The disclosures of said provisional applications are hereby incorporated by reference in their entirety.

FIELD OF THE INVENTION

The present inventions relate to the field of devices and systems for measuring, tracking, and actuating on sleep/wake and circadian rhythms via direct and indirect stimuli, including delivering certain agents and/or conditioned olfactory stimuli at specific times of day and specific times relative to scheduled sleep/sleep states to improve sleep and facilitate sleep hygiene.

BACKGROUND OF THE INVENTION

Circadian rhythms are endogenous biological rhythms that have a period of about twenty-four hours that allow the brains and bodies of a subject (e.g., a mammal) to anticipate and prepare for daily events (e.g., waking up, eating, sleeping). Circadian rhythms persist in the absence of external cues (e.g., solar light/dark cycle) and are entrainable (e.g., can be reset by exposure to stimuli, such as light). Circadian rhythms are displayed in the biology, physiology, and behaviors of most organisms on earth, including humans. For example, circadian rhythms favor sleep at certain times of day and wake at others and also influence a host of other physiologic and behavioral processes including alertness, performance, hormone production, metabolism, drug metabolism, cardiovascular functioning, etc. A functional circadian system is vital for optimal health, performance, and survival.

Core body temperature and dim light melatonin onset (DLMO) are commonly used markers for monitoring internal circadian phase or biological time (e.g., what time it is in the brain) in humans. In addition, monitoring sleep/wake patterns across days and weeks allows for the prediction/estimation of circadian phase. When internal circadian time is aligned to the external environment, physiological and behavioral processes are enhanced (e.g., enhanced or improved sleep, cognitive and physical performance, alertness, metabolism, and gastrointestinal function); however, when the internal circadian timing system and external environment are misaligned (e.g., due to shiftwork or jetlag) a host of physiological and behavioral processes are negatively impacted.

Several stimuli have direct and indirect influence on circadian rhythms, sleep, and performance (e.g., light and melatonin) and the appropriately timed (e.g., circadian phase, time relative to sleep or wake, and time relative to scheduled performance) administration of such stimuli, for example, can shift circadian biology to better match the external environment thereby enhancing performance, alertness, mood, sleep, etc. of a subject. The appropriately timed delivery of these stimuli is paramount. The administration of circadian-targeted stimuli (e.g., light and melatonin) can have an undesired outcome (e.g., decreased performance, alertness and/or disrupted sleep) if administered at the incorrect time/phase.

Needed are new strategies, devices and methods for estimating or determining the circadian phase of a subject (e.g., a human subject). Also needed are new strategies, devices and methods of delivering to a subject certain sleep, circadian and/or performance enhancing stimuli to enhance sleep and/or align circadian biology to an external environment (e.g., the subject's present environment or an anticipated environment). Insufficient sleep and sleep disruption negatively impact awake time functioning, quality of life, and both physical and mental health. Improving one's sleep is critical for professionals who operate in adverse environments, such as military personnel, astronauts, truck drivers, night shift employees, and individuals stationed in noise prone environments. Improving one's sleep becomes particularly difficult when it depends on improving the sleep of another person first or environmental factors out of their control (noise, light, etc.). For example, military personnel (e.g., during combat) and new parents experience significant disruption to sleep quality and amount, as well as parents of children with autism or other children with special needs. One of the major issues in pediatric populations, as well as some adult populations, is a lack of non-pharmaceutical based sleep aids that are safe to use in newborns or in children with autism who are already on other medications, for example. Thus, also needed are minimally invasive, safe and effective systems to improve sleep in populations while being capable of acquiring feedback and performing adjustment and customization for different subjects and changing environments or activity patterns.

SUMMARY OF THE INVENTION

Disclosed herein are novel compositions, devices, systems and methods useful for estimating and/or determining the circadian phase of a subject by the continuous monitoring and/or tracking of consciousness patterns (e.g., sleep/wake patterns) of the subject. The consciousness patterns (comprising sleep and/or wake pattern data) monitoring and circadian phase estimations are used to appropriately determine and time the delivery of sleep, circadian, and performance agents. Sleep, circadian, and performance agents may include or comprise, for example, stimulants, such as caffeine, performance enhancing stimuli, such as, for example, steroids, sleep inducing agents, such as sedatives (e.g., sleeping pills) or phase shifting medications/stimuli, such as melatonin or light. Delivery of such agents (e.g., circadian agents) at the appropriate time(s) serve to align the subject's circadian biology to the external environment. The result of aligning the subject's circadian biology with the external environment is the enhancement of the subject's physiological and cognitive processes.

Certain embodiments disclosed herein are directed to devices, patches and systems for determining, estimating, monitoring and/or tracking one or more of activity patterns, inactivity patterns, polysomnographic patterns and circadian states of a subject. Additionally, the devices, patches or systems include or comprise a microcontroller, volatile and non-volatile memory, a communications interface, and a battery, one or more electrical pads configured to contact skin of the subject and collect and monitor polysomnographic data for the subject, one or more actuating devices configured for controlled transdermal delivery of one or more agents that alter circadian rhythm, sleep and/or alertness state of the subject through at least one nozzle, and a container encasing the microcontroller, the volatile and non-volatile memory, the communications interface, the battery, the one or more electrical pads, the one or more actuating devices, and the at least one nozzle.

In some embodiments, such devices, patches and systems further include or comprise a flexible circuit board with the microcontroller, the volatile and non-volatile memory, the communications interface, the battery, the one or more electrical pads, and the one or more actuating devices embedded thereon. In some aspects, the flexible circuit board is coated with impermeable resin or other material to prevent damage from moisture. In some embodiments, monitoring polysomnographic data comprises measuring polysomnographic data selected from the group consisting of brainwave data, eye movement data and muscle tone data, collected from one or more patch mounted sensors, and activity/inactivity patterns are monitored by one or more sensors measuring rest and activity cycles via actigraphy. In some aspects, the one or more electrical pads are further configured to measure at least one of skin temperature and blood oxygen saturation levels of the subject. In still other embodiments, the one or more electrical pads are further configured to sense pulse/blood oximetry and analyze sweat and other skin secretions of the subject.

In certain embodiments, the devices, patches and systems disclosed herein are configured to be worn on the skin of a subject, and the container further includes a breathable polymer or fabric that allows the skin of the subject to breathe while maintaining close contact with the skin of the subject. In certain aspects, such polymer or fabric may also act as an occlusive material to facilitate the transdermal absorption of one or more agents. In some aspects, the container further includes a skin-compatible adhesive to adhere the patch to skin of the subject. In still other embodiments, the container further includes a conductive gel or adhesive to increase conductivity of skin of the subject and the one or more electrical pads.

In certain aspects, the devices, patches and systems disclosed herein include or comprise a communications interface configured to communicate with other patches, and/or transfer measured and calculated data to be stored at or by other patches containing memory, and/or trigger the delivery of stimuli in other patches that are capable of delivering such stimuli. For example, such a communications interface may communicate with the other patches by applying low power electrical signals to the skin of the subject such that the signals propagate on the surface of the skin to the other patches.

In certain aspects, the container of the devices, patches and systems disclosed herein further include or comprise a vessel capable of storing various doses of an agent to be delivered transdermally to the subject by the one or more actuating devices. Similarly, in other aspects the devices, patches or systems disclosed herein further include or comprise photodiodes configured to measure environmental light exposure, and for estimating the total light dosage (e.g., stimulus content) received by the subject over a period of time, wherein a specific time relative to sleep onset, offset, or estimated circadian phase at which the light stimuli were received can also be derived from these measurements.

The devices, patches and systems disclosed herein may be configured to deliver one or more agents, for example, one or more agents selected from the group consisting of a central nervous system depressant and a central nervous system stimulator. In certain aspects, the one or more agents modulate the circadian biology of the subject. In certain aspects, the one or more agents include or comprise one or more central nervous system depressants (e.g., a central nervous system depressant selected from the group consisting of an opioid, a hypnotic, a benzodiazepine, a barbiturate, a sleeping medication, a pain medication, and combinations thereof). In certain aspects, the one or more agents include or comprise one or more phase shifting medications/stimuli, (e.g., melatonin or light). In certain aspects, the one or more agents include or comprise one or more central nervous system stimulants (e.g., a central nervous system stimulants selected from the group consisting of light, caffeine, modafinil, methylphenidate and combinations thereof). In some embodiments, the one or more agents include or comprise combinations of one or more central nervous system depressants, one or more phase shifting stimuli, and one or more central nervous system stimulants.

Also disclosed herein are methods and systems of modulating the circadian phase of a subject in response to the subject's environment, such methods and systems comprising steps of: initializing a wearable skin-patch positioned on skin of a subject, the patch comprising a microcontroller, a volatile and non-volatile memory, a communications interface, a battery, one or more electrical pads, one or more actuating devices, and at least one nozzle, collecting and monitoring sleep/wake/polysomnographic data, by the one or more electrical pads, of the subject, estimating or determining, by the microcontroller, a circadian phase of the subject based on the collected and monitored activity/inactivity patterns polysomnographic data, and delivering one or more agents, through at least one nozzle in controlled transdermal delivery, by the one or more actuating devices, to the skin of the subject based on the estimated or determined circadian phase, wherein the delivery of the one or more agents modulate the circadian phase of the subject in response to the subject's environment. Delivery of the one or more agents may be provided at a specific time relative to sleep/wake based on collected or historical data or during a specific sleep state (e.g., relying upon sensor input and data, such as from polysomnography) or delivery of the one or more agents may be provided at a specific circadian phase (e.g., based upon monitored sleep/wake patterns).

In certain aspects of the foregoing methods and systems, the one or more agents are selected from the group consisting of one or more central nervous system depressants and one or more central nervous system stimulants. In certain aspects of the foregoing methods and systems, the one or more agents include or comprise one or more central nervous system depressants (e.g., one or more central nervous system depressants selected from the group consisting of an opioid, a hypnotic, a benzodiazepine, melatonin and combinations thereof). In certain embodiments, the one or more agents include or comprise one or more central nervous system stimulants (e.g., light, caffeine, modafinil, methylphenidate and combinations thereof).

In certain aspects of the foregoing methods, the agent is or comprises an olfactory agent. Olfactory agents comprise non-invasive, effective non-pharmaceutical based sleep, wake, energy and/or relaxation enhancers that are safe to use in humans including vulnerable populations (e.g., newborns, children with autism, and/or those who are already on other medications). The result of enhancing sleep, enhancing alertness, aligning the subject's circadian biology with the external environment is a system that improves sleep in populations that cannot or prefer not to use pharmaceutical interventions, shifting of timing of sleep, adjusting circadian phase, enhancing alertness, enhancing performance, reducing sleep onset latency, enhancing sleep consolidation and reducing variability in sleep patterns, adjusting mood and enhancing physiological processes. For example, olfactory agents can be automatically dispensed at specific times of day or specific times relative to sleep/wake to facilitate at least one action selected from the group consisting of sleep, wake, increased energy, and relaxation. Delivery of such agents sets a sleep-and-wake schedule for the subject and, in certain embodiments, specific olfactory agents may be specifically assigned to activity events selected from the group consisting of bed time, rise time, nap time, awake time and combinations thereof. In certain aspects, the systems and inventions disclosed herein use algorithms to avoid habituation to agents (e.g., olfactory agents) relative to onset of activity events.

In certain aspects of the devices, patches, systems and methods disclosed herein, the subject is a mammal, more specifically a human subject (e.g., an adult, an elderly adult, an adolescent or an infant).

Certain example embodiments of the present invention disclosed herein are directed to a system for adjusting consciousness patterns (comprising sleep and/or wake pattern data) and circadian states of one or more subjects. For example, in certain aspects the system includes an olfactory dispensing unit configured to dispense olfactory agents, a control unit, a user interface and a set of sensors. The control unit configured to actuate the olfactory dispensing unit and store data from one or more sensors configured to perform one or more functions selected from the group consisting of estimating and tracking activity and inactivity data for the one or more subjects, measuring a presence then concentration of olfactory agents, collecting and monitoring consciousness patterns data for the one or more subjects, and quantifying measurements of circadian outcomes for the one or more subjects. The user interface receives control commands, input from a user (e.g., the subject), for using the control unit to actuate the olfactory dispensing unit to dispense the olfactory agents. The olfactory dispensing unit and the control unit are configured to be in electronic communication, and the user interface and the control unit are configured to be in electronic communication. The system dispenses the olfactory agents to modulate a circadian phase and consciousness state of the one or more subjects in response to a condition of the one or more subjects and an environment of the one or more subjects.

In accordance with aspects of the present invention, the olfactory dispensing unit can be one or more containers that store the olfactory agents, and one or more actuators that dispense the olfactory agents into the environment of the one or more subjects.

In certain aspects of the present invention, the control unit can actuate the olfactory dispensing unit as a function of time, according to a formulation, using a timing device configured to keep time. The control unit can use memory to store the olfactory formulation and data from the one or more sensors and other system components, using a processor to compute relevant parameters and adjust the formulation in real-time to control timing indicating when olfactory agents are dispensed and amounts indicating how much olfactory agents are dispensed (e.g., indicating the volume of olfactory agents dispensed). The olfactory dispensing unit can be configured to dispense olfactory agents using an actuator that uses at least one mechanism selected from the group consisting of electrical heating of olfactory agents comprising one or more liquids actuated by the control unit at specific times designated by the formulation to cause evaporation, ultrasonic nebulizers comprising a vibrating transducer actuated by the control unit, one or more solids in contact with a heating element actuated by the control unit at specific times designated by the formulation to facilitate delivery of olfactory agents, ultrasonic nebulizers comprising a vibrating transducer actuated by the control unit, air-stream atomizers comprising an air-stream generator actuated by the control unit, and volatile substances stored in a container that is opened and closed by the control unit to allow and prevent vapors of the olfactory agents to propagate out of the olfactory dispensing unit into the environment of the one or more subjects.

In certain aspects of the present invention, the olfactory agents can modulate sleep, alertness, and/or circadian biology of the one or more subjects.

In certain aspects of the present invention, the one or more sensors can be configured to perform collecting and monitoring of consciousness patterns data for the one or more subjects. The monitoring of consciousness patterns data can include or comprise using the sensors to quantify the sleep and circadian patterns of the one or more subjects by sensing at least one signal, which at least one signal may be selected from the group consisting of rest and activity cycles using actigraphy, signals using polysomnography, skin temperature, sleep onset time and duration, environmental light exposure, total light dosage received by the one or more subjects over a period of time, pulse oximetry, blood oxygen saturation levels, sweat and other skin secretions of the one or more subjects, and biofeedback signals indicative of sleep patterns of the one or more subjects.

In certain aspects of the present invention, the control unit can reference, use or otherwise rely on consciousness pattern data of each of the one more subjects to optimize a formulation of the olfactory agents in real-time to provide cues to achieve a stimuli response in each of the one or more subjects. The stimuli response can be one or more actions selected from the group consisting of shifting of timing of sleep, adjusting circadian phase, enhancing alertness, enhancing performance, reducing sleep onset latency, enhancing sleep consolidation and reducing variability in sleep patterns and adjusting mood.

In certain aspects of the present invention, the system can include or comprise at least one smart olfactory dispensing unit and software that tracks sleep history information of the one or more subjects, then sets a sleep-and-wake schedule for the one or more subjects and designates specific olfactory agents assigned to activity events selected from the group consisting of bedtime, risetime, nap time, awake time and combinations thereof. The olfactory agents can be automatically dispensed at specific times of day to facilitate at least one action selected from the group consisting of sleep, wake, increased energy, and relaxation. The system uses algorithms to avoid habituation to olfactory agents relative to onset of activity events.

In certain aspects of the present invention, the one or more sensors can be configured to sense the environment of the one or more subjects by directly measuring the concentration of olfactory agents in the air of the environment of the one or more subjects, allowing the system to control a quantity of olfactory agents present in the environment of the one or more subjects. The one or more sensors can include or comprise a sensor selected from the group consisting of sensors configured for estimating concentrations in air for certain specific gases, sensors configured for estimating concentrations in air for volatile organic compounds, sensors that map aromas to images and combinations thereof.

In certain aspects of the present invention, a formulation can include or comprise a list of times and desired concentrations of the olfactory agents at each time. The concentrations of olfactory agents for use in the formulation can be determined from measured amounts of the olfactory agents absorbed by the one or more subjects over a certain exposure period. The concentrations of olfactory agents for use in the formulation can be measured using absolute units, empirical units and combinations thereof.

In certain aspects of the present invention, the control unit can actuate the olfactory dispensing unit to dispense olfactory agents with output and intensity based upon measurements of circadian outcomes and application of machine learning techniques to indirectly infer adequate concentrations of a formulation and the olfactory agents in an environment of the one or more subjects.

In certain aspects of the present invention, the olfactory dispensing unit and the control unit both can be contained within a physical device that further comprises a smart plug and wireless communication unit, and wherein a formulation is stored in memory of the control unit controlling dispensing of the olfactory agents. The control unit can be controlled remotely using wireless electronic communication sent from a separate device comprising the user interface configured to receive input from the user (e.g., a subject) to modify parameters of the system and adjust the formulations.

In certain aspects of the present invention, the control unit can be physically separated from the olfactory dispensing unit and communicates electronically with the olfactory dispensing unit using wired or wireless technologies. The control unit can use processors, memory and dedicated software that control the system and the control unit is physically connected to the user interface configured to receive input from the user (e.g., a subject) to modify parameters of the system and adjust the formulations.

In certain aspects of the present invention, the control unit, the olfactory dispensing unit and the one or more sensors can communicate electronically using transceivers, wireless communication units and wireless routers configured to operate using wireless technology standards selected from the group consisting of Bluetooth®, Bluetooth® low energy (BLE), Zigbee®, Wi-Fi®, infrared, near field communication and combinations thereof.

In certain aspects of the present invention, the system can include or comprise a fan, configured to circulate air through the system.

In certain aspects of the present invention, the olfactory agents can include or comprise one or more agents that can be central nervous system depressants or central nervous system stimulators.

In certain aspects of the systems and methods disclosed herein, the subjects are mammals (e.g., humans).

In certain aspects of the present invention, one or more sensors can include or comprise a skin-compatible adhesive to adhere the one or more sensors to skin of the one or more subjects.

Also disclosed herein are devices, systems and methods of modulating and adjusting consciousness patterns and circadian states of one or more subjects in response to the subjects' environment, such devices, systems and methods comprising steps of: providing an olfactory dispensing unit; actuating the olfactory dispensing unit using a control unit, and storing data from one or more sensors; performing, using the one or more sensors, a function selected from the group consisting of estimating and tracking activity and inactivity data for one or more subjects, collecting and monitoring consciousness patterns data for one or more subjects, and quantifying measurements of circadian outcomes for one or more subjects; inputting, using a user interface, control commands for using the control unit to actuate the olfactory dispensing unit to dispense the olfactory agents; electronically communicating, between the olfactory dispensing unit and the control unit and between the user interface and control unit; and dispensing of the olfactory agents, thereby modulating sleep/wake and/or a circadian phase of the one or more subjects in response to a condition of the one or more subjects and an environment of the one or more subjects.

In certain aspects of the foregoing devices, systems and methods, the one or more sensors are configured to collect and monitor consciousness patterns data of the one or more subjects. The monitoring consciousness patterns data can comprise using the one or more sensors to quantify the sleep and circadian phase/rhythms of the one or more subjects by sensing at least one signal selected from the group consisting of rest and activity cycles using actigraphy, signals using polysomnography, skin temperature, sleep onset time and duration, environmental light exposure, total light dosage received by the one or more subjects over a period of time, pulse oximetry, blood oxygen saturation levels, sweat and other skin secretions of the one or more subjects, and biofeedback signals indicative of sleep patterns of the one or more subjects. The control unit can use consciousness patterns data of each of the one more subjects to optimize a formulation of the olfactory agents in real-time to provide cues to achieve a stimuli response in each of the one or more subjects. The stimuli response can include or comprise one or more actions selected from the group consisting of shifting of timing of sleep, reducing sleep onset latency, enhancing sleep consolidation and reducing variability in sleep patterns.

In certain aspects of the foregoing devices, systems and methods, the control unit can actuate the olfactory dispensing unit as a function of time, according to a formulation, using a timing device configured to keep time. The control unit can use memory to store the formulation and data from the one or more sensors and other system components, using a processor to compute relevant parameters and adjust the formulation in real-time to control timing when the olfactory agents are dispensed and amounts indicating a quantity of the olfactory agents to dispense. The olfactory dispensing unit can be configured to dispense the olfactory agents using an actuator that uses at least one mechanism selected from the group consisting of electrical heating of olfactory agents comprising one or more liquids actuated by the control unit at specific times designated by the formulation to cause evaporation, ultrasonic nebulizers comprising a vibrating transducer actuated by the control unit, air-stream atomizers comprising an air-stream generator actuated by the control unit, and volatile substances stored in a container that is opened and closed by the control unit to respectively allow and prevent vapors of the olfactory agents to propagate out of the olfactory dispensing unit and into the environment of the one or more subjects.

The above discussed, and many other features and attendant advantages of the present inventions will become better understood by reference to the following detailed description of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
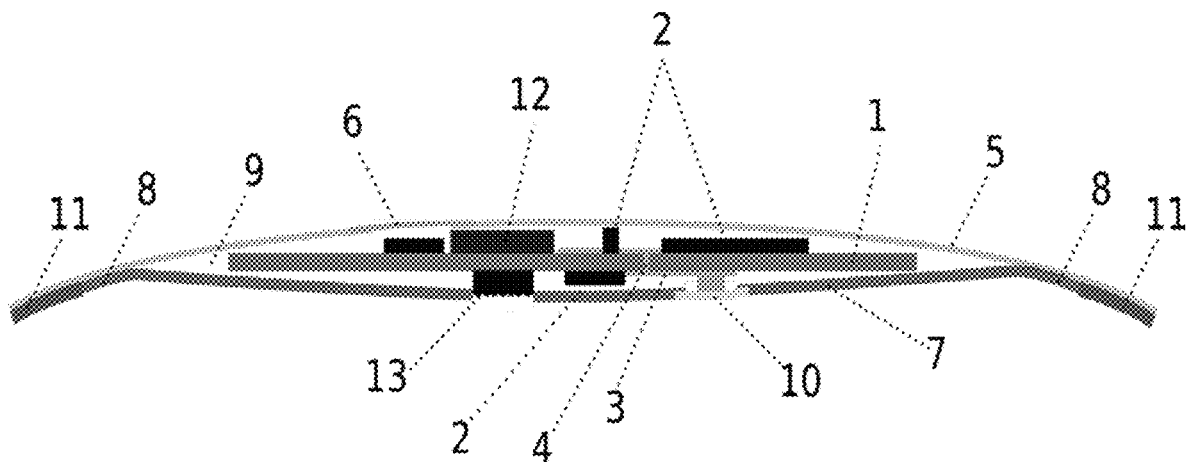
FIG. 1 depicts a side/cross section view of the device.
Figure 2:
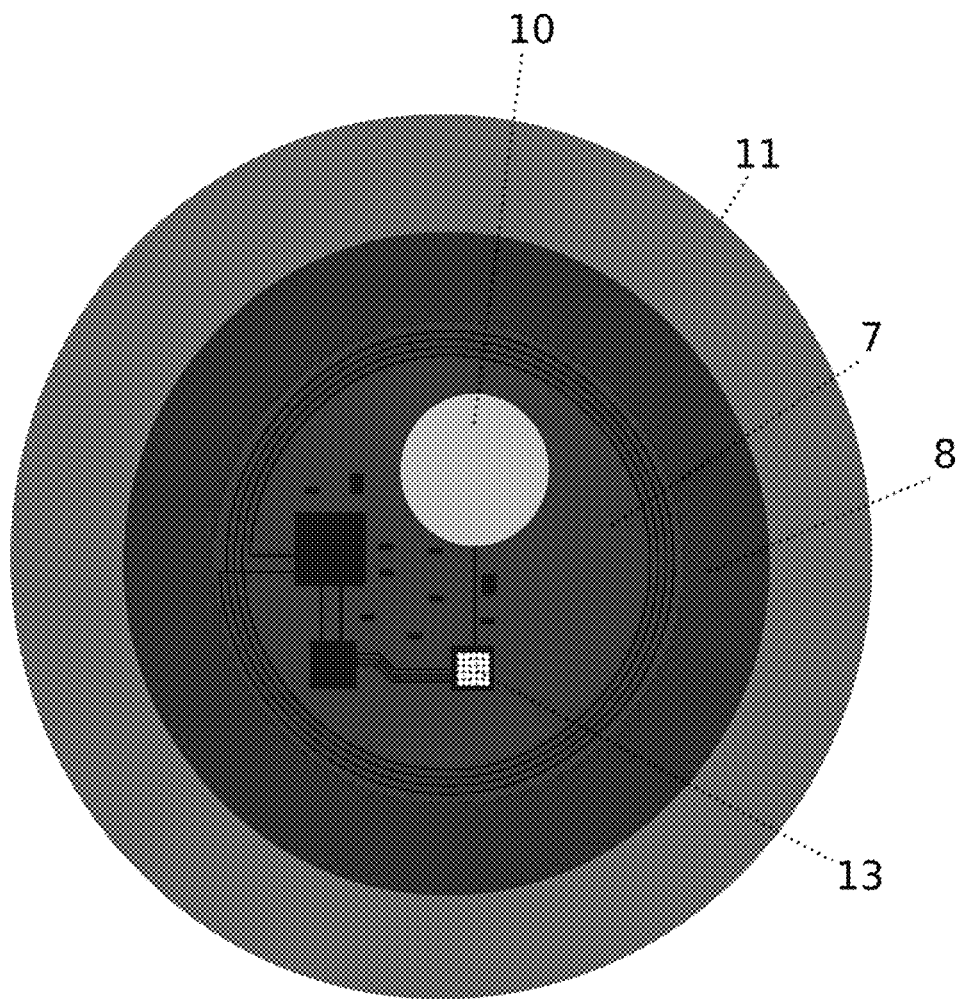
FIG. 2 illustrates a bottom view of the patch, showing a (set of) contact(s) (yellow) for measuring electrical signals on the skin, as well as the nozzles for the substance dispenser.
Figure 3:
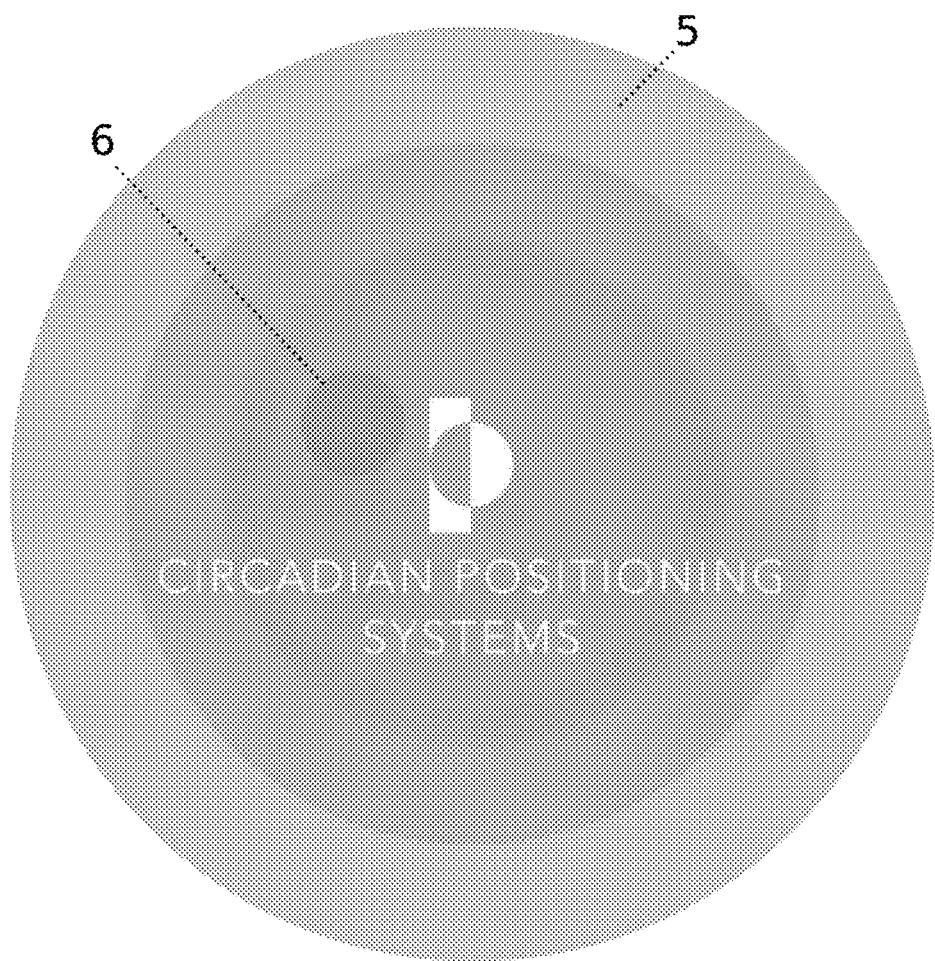
FIG. 3 illustrates a top view of the patch (ambient side). The transparent outward facing window allows for the measurement of light levels (lux) and color/spectral composition.

An illustrative embodiment of the present invention relates to compositions, devices, systems and methods for adjusting (e.g., advancing, delaying, stabilizing, etc.) consciousness patterns (comprising sleep and/or wake pattern data) and circadian states of one or more subjects. In certain embodiments, the subject inventions are directed to wearable skin-patches and related systems for determining and/or estimating and tracking a subject's sleep/wake patterns and circadian state, as well as for administering timed agents (e.g., stimuli) with the object of shifting and/or aligning the subject's circadian state to external schedules based on measured data and smart algorithms. In certain aspects, the patches and systems disclosed herein include or comprise patches that are worn on the skin of a subject. In certain embodiments, the patches and systems described herein comprise, include or comprise or are equipped with one or more different sensors and actuator devices, a microcontroller, volatile and non-volatile memory for storing program code and measured data, a communications interface, wired or wireless, that allows for data to be transferred from the patches to a computer, tablet or phone, a real-time clock for providing timestamps for the measurements, and a battery, which can be rechargeable or not. In certain embodiments, the system uses a control unit to control a dispensing unit to dispense olfactory agents in specific quantities over specific time durations together with sensors that provide data about the subjects and environment for estimating and tracking subject activity (e.g., sleep/wake), collecting and monitoring consciousness patterns of subjects and quantifying circadian outcomes of subjects, wherein the system comprises a user interface for users to input commands to the control unit, which is in electronic communication with the components of the system to modulate a circadian phase and consciousness state or consciousness pattern (comprising sleep and/or wake pattern data) of the one or more subjects by dispensing quantities of the olfactory agents over time in response to a condition of the one or more subjects and an environment of the one or more subjects. The novel compositions, devices, systems and methods are useful for estimating and/or determining the circadian phase of a subject by the continuous monitoring and/or tracking consciousness patterns of a subject. These sleep/wake pattern monitoring and circadian phase estimations are used to appropriately determine and time the delivery of olfactory agents for promoting sleep, circadian phase, and performance. In certain embodiments, the agents may comprise one or more sleep, circadian, and performance agents, for example, stimulants, such as caffeine, performance enhancing stimuli, such as, for example, steroids, sleep inducing agents, such as sedatives (e.g., sleeping pills) or phase shifting medications/stimuli, such as melatonin or light. Delivery of such agents (e.g., olfactory agents) at the appropriate time aligns the subject's circadian biology to the external environment. The result of directly enhancing sleep/wake and/or aligning the subject's circadian biology with the external environment is the enhancement of physiological and cognitive processes. Unlike other systems that employ drugs to adjust consciousness patterns, this system accomplishes adjusting consciousness patterns (comprising sleep/wake pattern data) and circadian states of one or more subjects using safer olfactory agents.

In certain embodiments, patches with different functions include or comprise the devices, systems and methods of modulating and adjusting consciousness patterns and circadian states of one or more subjects in response to the subjects' environment disclosed herein. In certain aspects of the foregoing patch devices, systems and methods, one or more sensors are configured to perform these different functions to collect and monitor consciousness patterns data of the one or more subjects. In some embodiments, these functions include or comprise monitoring a subject's rest and activity cycles via actigraphy (movement measurement with an accelerometer), measuring environmental light exposure with photodiodes or other light sensitive devices, collecting and monitoring polysomnographic data (e.g., electroencephalogram, electrooculogram, and electromyogram, and electrocardiogram) via electrical pads that contact the subject's skin, measuring the subject's skin temperature, and/or measuring the subject's blood oxygen saturation levels. In certain aspects, the patch systems disclosed herein also allow for timed (e.g., both time of day, time relative to sleep, and/or circadian phase) transdermal delivery of one or more agents (e.g., natural substances) that alter or otherwise modulate circadian rhythm (e.g., agents such as caffeine and melatonin), as well as for transdermal sensing, such as pulse/blood oximetry and analysis of sweat and other skin secretions of the subject (e.g., for hormones or metabolites that may contain information relevant for the assessment and manipulation of circadian rhythms and sleep patterns). The monitoring consciousness patterns data can include or comprise using the one or more sensors to quantify the sleep and circadian system of the one or more subjects by sensing at least one signal selected from the group consisting of rest and activity cycles using actigraphy, signals using polysomnography, skin temperature, sleep onset time and duration, environmental light exposure, total light dosage received by the one or more subjects over a period of time, pulse oximetry, blood oxygen saturation levels, sweat and other skin secretions of the one or more subjects, and biofeedback signals indicative of sleep patterns of the one or more subjects. The system can use consciousness patterns data of each of the one more subjects to optimize manipulation of circadian rhythms and sleep patterns in real-time to provide cues to achieve a stimuli response in each of the one or more subjects. The stimuli response can include or comprise one or more actions selected from the group consisting of shifting of timing of sleep, reducing sleep onset latency, enhancing sleep consolidation, reducing variability in sleep patterns, reducing fatigue and increasing alertness and focus. The internal memory of the patch possess the capability to download a tapered dosage plan to be implemented at controlled intervals using intervention schedulers rather than simply receiving a signal from sensors/external sources at the appropriate interval to administer the appropriate dosage based on measured response. Additionally the patch/device can contain program logic to derive intervention schedules without having to communicate to an external computer. An array of one or more patches may also be controlled by the means of communication via one or more external computers (including one or more central computers) to initiate or adjust delivery of agents in an integrated and coordinated manner.

In some embodiments, the patch includes a flexible circuit board with a microcontroller, memory (for program and data storage), real-time clock, sensors, battery, antenna, and a means of communicating with and transfer data to the external world, which could be wired (e.g., USB, UART, CAN, SPI, I2C, etc.) or wireless (e.g., Bluetooth, BLE, RF, Zigbee, WiFi, RFID, etc.). In certain embodiments, the circuit components may be coated with impermeable resin or other material to prevent damage from moisture.

In certain embodiments, an envelope or pouch container comprising or made at least partially of a breathable polymer or fabric, or other material that allows the subject's skin to breathe while maintaining close contact with the subject's skin is used to house and protect the circuit board. In certain embodiments, a skin-compatible adhesive attaches the device to the skin of a subject.

In certain embodiments, for certain applications the devices, systems and methods disclosed herein may include or comprise a conductive gel or adhesive for increasing the conductivity of the subject's skin when measuring electrical signals generated by the subject's brain, eyes, muscles, or the heart.

In certain aspects, the device, systems and methods disclosed herein include or comprise one or more sensing electrodes, terminals and/or probes on the device-skin interface and that may be used to allow measurements to be conducted onto the subject's skin surface. In certain embodiments, the devices, systems and methods disclosed herein (e.g., a patch) may communicate with other patches either wirelessly or via very thin wires. For wireless communication both short (e.g., RFID) and long range (e.g., BLE, WiFi and/or Zigbee) technologies may be used. Alternatively, low power electrical signals of certain frequencies applied to the skin and propagate on the surface of the subject's skin may be used by patches to communicate with other patches (e.g., other patches worn by the subject).

In one preferred embodiment, the patch includes or is equipped with sensors to measure actigraphy and/or response time. In such embodiments, the sensors may include or comprise an accelerometer for measuring a subject's movement, and a thermometer, for measuring the subject's skin surface temperature. In certain aspects, the devices (e.g., a patch) disclosed herein may include or comprise one or more or an LED, pushbutton or capacitive touch sense pad for measurement of a subject's reaction times (e.g., modified psychomotor vigilance task). Alternatively, in certain aspects the pushbutton/pad may be substituted by detection of finger tapping motion via the accelerometer. The one or more sensors may be physically or electrically connected in a variety of configurations known to persons of ordinary skill in the art. In certain aspects, sensors may be part of the patch as a component of the same physical package, wherein the sensors connect to the patch microcontroller via wires or physical placement on the same circuit board. In this configuration the sensors receive power from the same power pack that powers the patch (comprising a battery, etc.). In certain other aspects one or more sensors may be external (not connected to the patch) or stand-alone components, connected to the system or the patch via one of the wireless protocols described herein or known to persons of ordinary skill in the art. In this configuration sensors will be equipped with sensor-specific batteries or power supplies. More generally, sensor networking may be achieved via any one of various network topologies known to persons of ordinary skill in the art, including but not limited to: point to point, mesh, star, etc. Sensor networking depends on how the intervention scheduler is configured. If the scheduler runs on a central node/computer that processes the information gathered from various sensor nodes and then sends out commands/schedules to various devices, then a type of star topology is preferred. If, on the other hand, the schedule computation is done in the device itself, then a mesh or ring topology is preferred. In this latter case very small amounts of data are transferred between devices, mostly for the devices to check their schedule computations against the other devices and computers. Sensor data storage requirements also vary based on implementation. Where the patch is to compute sleep sleep/wake on the fly based on sensor data, store the minute by minute sleep states for the past few days, and then use that information to compute intervention schedules on the fly, small amounts of memory are required. This type of implementation is feasible as long as the algorithms for computing sleep state and deriving schedules are no too complex, and will only require the memory available within the microcontroller on e.g., a circuit board. If the algorithms are complex, then the patch's microcontroller will likely not have enough computational power to execute the algorithms. In this case a network solution is required, where the patch transmits sensor data to one or more central computers, which then perform the computations and returns the intervention schedules to the patches. In either embodiment, the patch controller comprises a built in real time clock that keeps track of time for timestamping sensor measurements, timing delivery of agents comprising dosages, etc. Each patch may perform data analysis and provide feedback, including intervention schedules and delivery of one or more agents, in a variety of ways including: using only the patch's microcontroller, using an array of patches and associated data, using a networked set of one or more central computers, and combinations thereof, where sensor data from the various sources may be integrated (using e.g., the means of communication detailed herein) to perform such tasks.

In another preferred embodiment, the patch design may include or comprise a transparent, outside facing window, through which certain environmental conditions, such as light levels (Lux), light dosage, and light color and/or light spectral information can be measured. In certain aspects, these measurements are collected using photometer/photodiode chips, on-chip filter colorimeters, reverse biased color LEDs, or on-chip spectrometers.

In another embodiment, the compositions and systems (e.g., a patch) disclosed herein contains electrodes that contact the subject's skin and house analog amplifiers that condition PSG signals measured on the surface of the subject's skin or scalp before they are processed and stored by the microcontroller. Various such electrode-containing patches may be attached to various points on the subject's body to capture specific signals relevant to PSG.

In certain embodiments, the compositions and systems (e.g., a patch) disclosed herein include or comprise a container capable of storing various doses of an agent (e.g., a central nervous system stimulant or depressant) known to influence or modulate a subject's sleep, circadian rhythms, and or performance, such as caffeine or melatonin, to be delivered transdermally in a timed manner, as determined by algorithms contained in the system and by parameters derived from previously collected data. For instance, activity counts may be collected by the subject patches and systems using an accelerometer and scored as sleep or wake in 1-minute intervals. Form these sleep/wake timing data, circadian phase and timing of biological day/night can be estimated. These estimates of biological day and night will be interpreted in combination with the desired timing of performance. One example of how algorithms are generated includes the knowledge of an individual subject's (or group of subjects') current location (e.g., Boston), location of destination (e.g., London, UK), and the amount of time until arrival at destination. In the current, example, London is 5 hours ahead of Boston, the subject's biological clock needs to be advanced (moved forward in time) in order for performance to be enhanced while in London. Thus, in such embodiments the patch and systems disclosed herein would administer melatonin the phase advance region of the melatonin and light in the phase advance portion of the phase response curve.

In certain aspects, the container is actuated via an electrical signal from the microcontroller to perform timed delivery of the agent onto the skin of the subject. Because certain agents such as caffeine and melatonin can be absorbed by the skin of a subject and do not need to be driven into the skin (e.g., via iontophoresis), in certain aspects the compositions and system described herein operate by delivering (e.g., spraying) a predetermined dose of caffeine onto the subject's skin and allowing the sprayed content to be absorbed by the skin.

Referring to FIG. 1, the circuitry of the patch is laid out on a flexible sheet material [1], such as pyralux, that allows the patch to conform to the contour of the region of the subject's body to which it is applied. In some embodiments, particularly where the circuitry can be contained in small device areas, a conventional hard printed circuit board may be used. Circuit components [2] are soldered to the copper, tin or silver tracks [3] on the pyralux or on the hard circuit board with lead-free solder. Electrical components and tracks may be placed on both sides of the pyralux sheet and the sides may be electrically connected with vias [4]. The circuitry may then be covered with a thin impermeable layer of acrylic or silicone polymer, or the entire device is placed in a sealed plastic or polymer envelope to protect the circuit elements from moisture and other environmental elements that could cause damage. Alternatively, the circuit and tracks may be printed with silver-based ink onto a thin and flexible film, such as polyethylene terephthalate (PET). The layer is then covered in acrylic or silicone to become impermeable to moisture.

On top of the flexible circuit board a protective sheet [5] may be used that can be made of woven fabric, plastic (PVC, polyethylene or polyurethane), or latex. The edges of the adhesive sheet extend beyond the edges of the circuit board. This sheet forms the outward facing side of the device, and serves to conceal and protect the device circuitry, as well as to provide a free adhesive border to attach the device to the skin. One or more transparent windows [6] may be fabricated onto this protective sheet, by cutting a hole on the sheet and then covering the hole with transparent flexible film material, such as polyethylene terephthalate (PET). Such windows allow light from the external environment to be captured by sensors placed on the printed circuit board.

On the bottom side of the flexible printed circuit board is a permeable fabric [7], such as cotton cloth or polyester, that may be used to allow the skin to breath and to absorb sweat. The edges [8] of the permeable fabric [7] are glued to the protective sheet [5] with a high tack adhesive to form a sealed pocket [9] that houses the circuit board [1]. Alternatively, the circuit board [1] is glued directly to the protective sheet [5] with high tack adhesive, and a bottom layer is not used, in which case the bottom of the circuit board [1] makes direct contact with the skin of a subject.

One or more contacts [10] may be attached on the permeable fabric bottom-layer [7] to allow measurement of electrical signals on the skin of a subject, such as for PSG applications. The contact pads are made of conductive material. In one example, the conductive pad is made of a piece of metal-clad pyralux or a thin, flexible copper film, coated with a thin layer of gold for passivation, and glued on the edges so as to cover a hole cut on the fabric bottom layer [7]. In another example, the contact pads [10] may be directly woven into the fabric bottom layer [7] with conductive yarn. Electrical contact to the contact pads is extended from the printed circuit board with wires, vias, or solder.

Adhesive [11], compatible with the skin of the subject (e.g., a human subject), is applied to the bottom of the device, either (preferably) only on the edges of the protective sheet [5] that are exposed (e.g., not covered by the permeable fabric bottom-layer [7]), or, in cases where the permeable fabric bottom-layer [7] is not used, on the entire bottom surface of the device.

In some applications, the bottom surface of the device, including the contact pads [10], that is not covered by adhesive may be coated with a conductive electrolyte solution/gel or other conductive substance to allow measurement of electrical signals on the skin.

For transdermal delivery of agents, such as caffeine and/or melatonin, the devices and/or patches disclosed herein may house a container [12] for storing such agents in either liquid/gel/foam form. A mechanism for actuating the container with electrical pulses may be used to control the delivery of the agents onto or into the skin of the subject. In certain embodiments, the mechanism for actuating the substance container consists of a piezo-actuated nozzle or set of nozzles [13], similar to those found on the cartridges of some inkjet printers, such as those produced by EPSON. Some other types of inkjet printers rely on a temperature actuated mechanism for dispensing a liquid agent, which involves heating the liquid to high temperatures and forming steam. In certain aspects, the selected temperature to which such agents are heated take into consideration whether the agents may be heat-labile (e.g., heating certain agents such as caffeine or melatonin solutions to produce steam that may degrade or alter the stability or efficacy of such agents).

In certain aspects, the nozzles [13] are positioned on the bottom face of the patch, preferably so that their exit surface stays slightly above the skin surface. When actuated a certain number of times by electrical pulses produced by the microcontroller, the nozzles spray a dose of the substance onto the skin of the subject. The precise dose amount is controlled via 1) the number of nozzles, 2) the rate at which the nozzle(s) dispense(s) the agent (e.g., a liquid agent) with each electrical pulse, 3) the number of pulses applied, 4) the dilution and composition of the agents loaded into the patches, and 5) the rate and efficiency with which the skin absorbs the agents.

Figure 4:
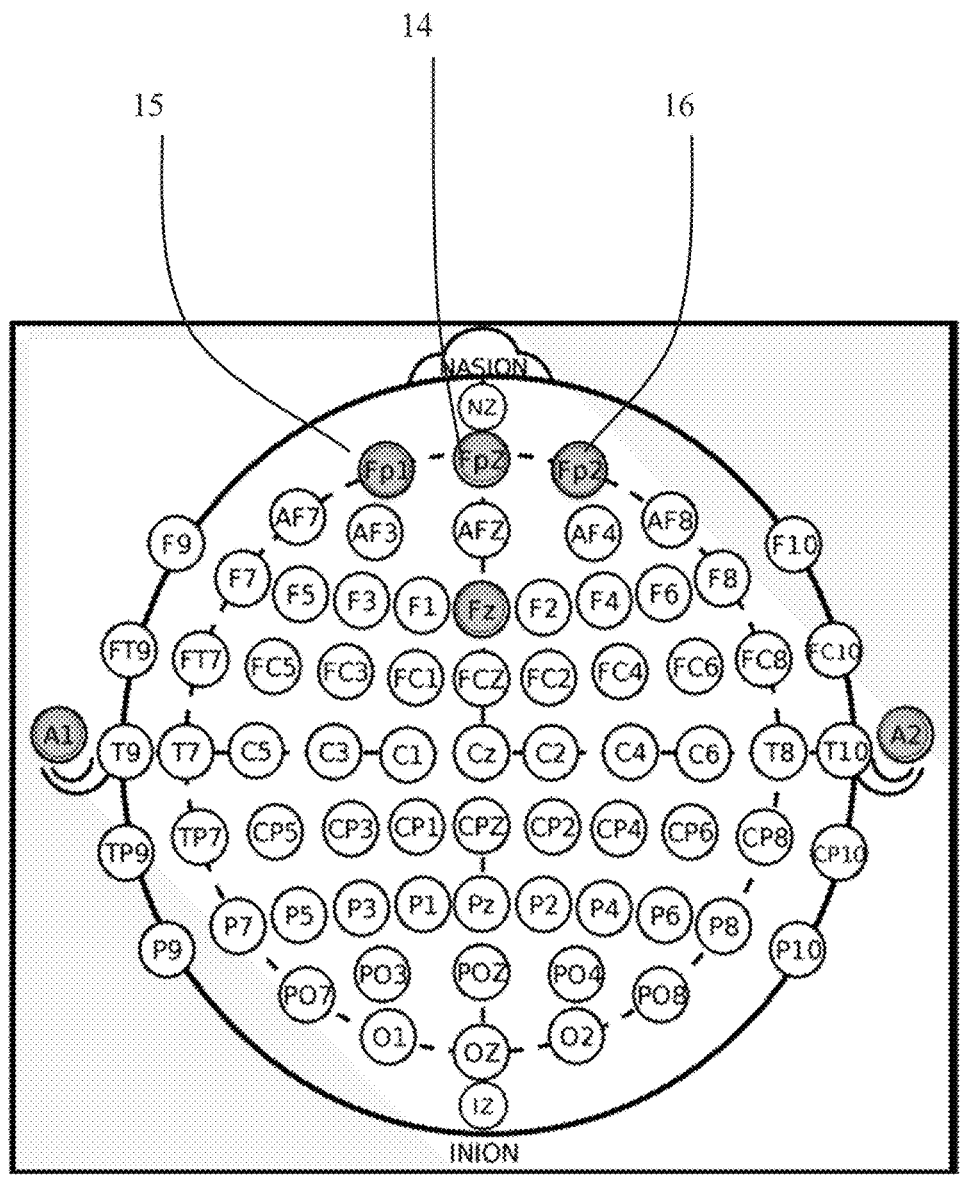
FIG. 4 illustrates commonly used positions for EEG electrodes, with preferred measurement points in the present inventions indicated by shading.

For measurement of electrical signals, particularly electroencephalographic or electrooculographic, electrodes are placed on different positions on the subject's head (scalp). One preferred positioning of the electrodes is indicated in FIG. 4, which shows the common locations for electrodes using the International 10-20 EEG placement system (Jasper, H. H. (1958). The ten-twenty electrode system of the International Federation. *Electroencephalography and Clinical Neurophysiology*, 10, 371-375, the entire contents of which are incorporated by reference herein.). In certain embodiments, not all of the electrode locations will be used by the present compositions and systems for determining sleep/wake state. In certain aspects, the electrodes of the present compositions and systems will include or comprise includes Fp1[15], Fp2 [16], Fz and reference electrodes FpZ [14], A1 and A2. Fp=Frontal pole, which is 10% from the nasion, based on the distance from nasion to inion. Fp1 and Fp2 are each 5% distance to the left (Fp1) or right (Fp2) Fp, based on the distance from pre-aricular to pre-aricular.

Figure 5:
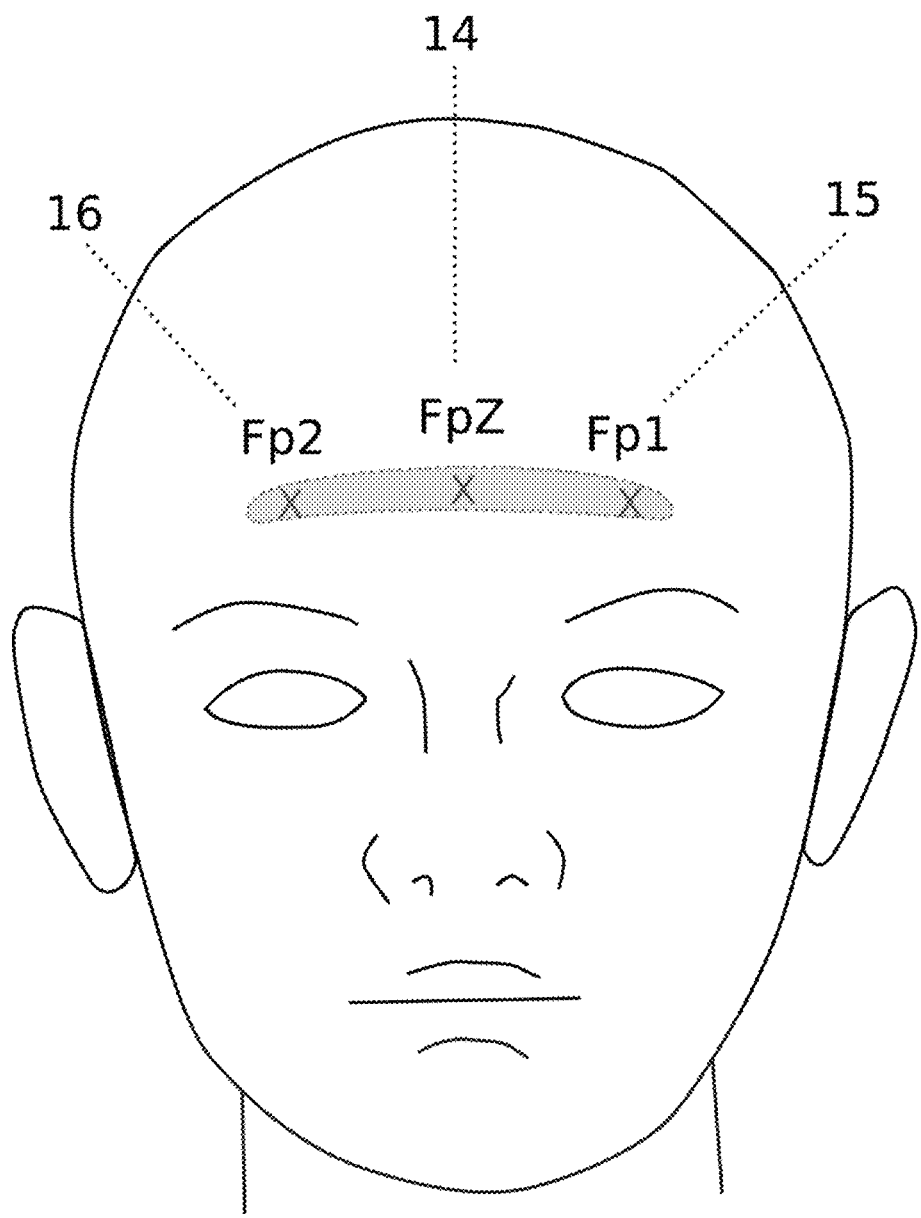
FIG. 5 depicts an outline (dashed curve) and electrode locations (red X's) for a patch that measures Fp1, Fp2, and FpZ on the forehead.

In some subject, the location Fz may be obstructed by hair. In certain embodiments, such as that depicted in FIG. 5, at least three electrodes are used—one of these being an active electrode located at Fp1 [15], another being an active electrode located at Fp2 [16] and the third being a reference electrode located at Fpz [14]. The colored/shaded region in FIG. 5 indicates a possible form for such a patch. The electronic components are not shown in the FIG. 5, and the electrode locations are indicated with an X.

Figure 6:
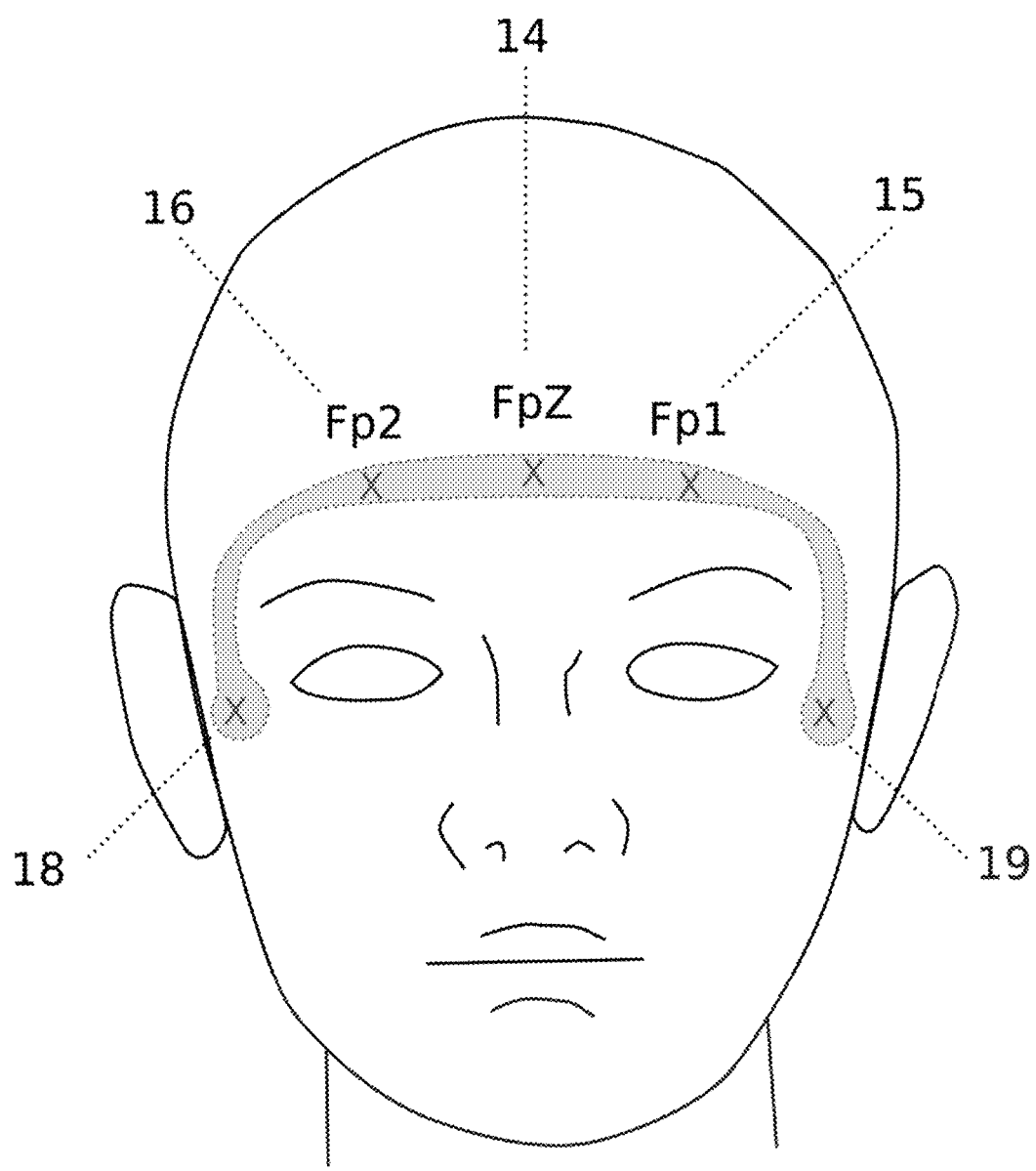
FIG. 6 depicts an outline and electrode locations for a patch that measures signals on the subject's forehead at locations Fp1, Fp2, and FpZ, as well as the subject's eye movement.

In some embodiments, the patches and devices disclosed herein can extend around the eyes of a subject to include or comprise electrodes [18] and [19] for capturing such subject's eye movements, as depicted in FIG. 6. In some embodiments, the subject's eye movement is detected by electrodes positioned on the outer canthi and placed slightly above or below the midline of the subject's pupil—[18] and [19], as illustrated in FIG. 6. Because these electrodes have to be referenced to the same voltage ground level, they must be electrically connected via physical conductor wires to the other electrodes to which they are referenced. This means that the patches and devices used in this type of measurement must extend and connect all of the involved electrodes, rather than comprising physically (and electrically) isolated patches.

Figure 7:
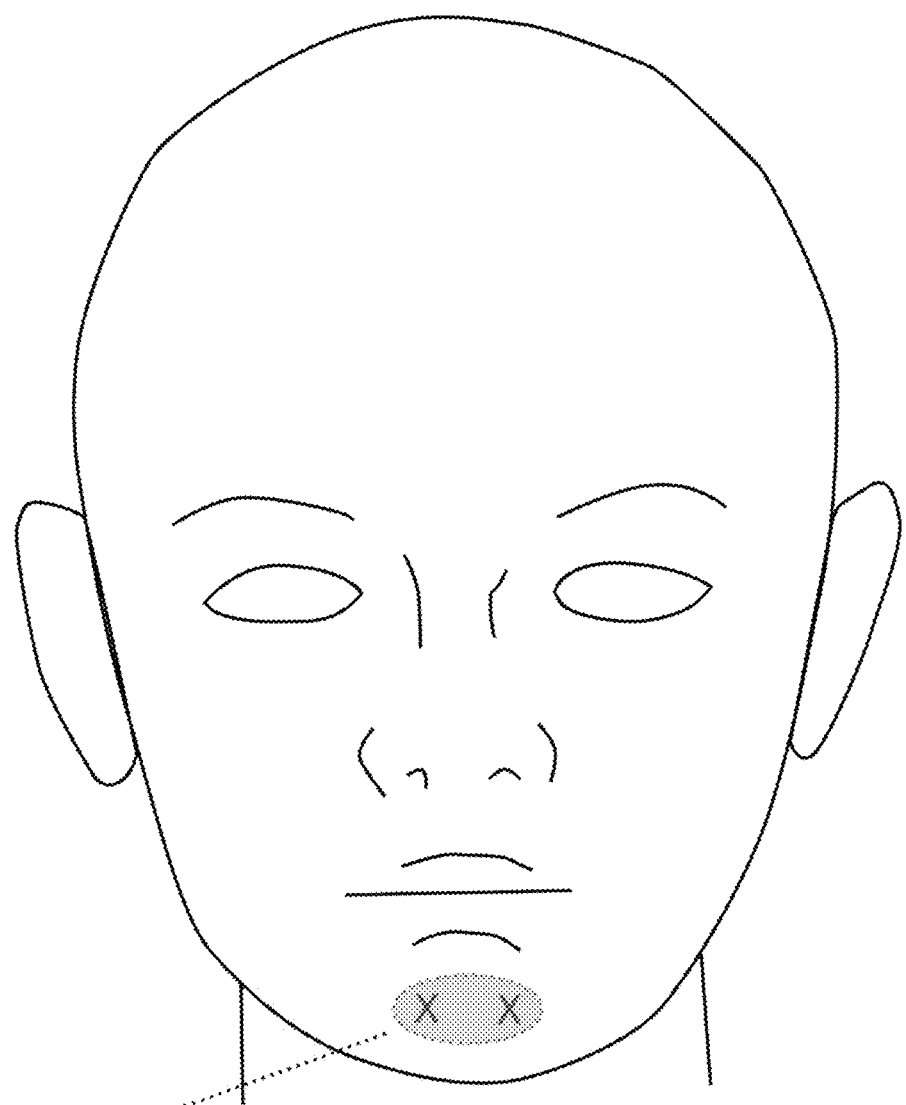
FIG. 7 illustrates an outline and electrode locations for a patch that measures a subject's chin muscle movements.

In another preferred embodiment, electrodes positioned on the chin, [17] as indicated in FIG. 7, are used to measure muscle movement.

In one embodiment, the subject inventions include or comprise one or more patches that can be deployed in a military population (e.g., ARMY, NAVY, AIR FORCE, etc.) to track a subject's sleep duration and frequency, and to estimate the subject's circadian phase and administer one or more agents (e.g., stimulants or sedatives or sleep/circadian stimuli) in order to prepare the subject for mission critical work.

In some aspects, the subject inventions include or comprise one or more patches can be deployed in a medical setting on subject for whom chronotherapy would reduce the side effects of certain medications or where administration of medication is more desirable during sleep (e.g., sleeping pill) or during a particular state of sleep (e.g., hormones).

In some aspects, the subject inventions include or comprise one or more patches that can be deployed in space on astronaut subjects in a similar capacity to that in military personal. Patches can be deployed in pediatric populations that have been historically difficult to study due to available technology to track sleep (e.g., babies or children with autism).

In some embodiments, the subject inventions include or comprise one or more patches that can be deployed in any individual subject whom performing well at various circadian phase and various intervals of time awake is important (e.g., businessmen, professional athletes, Olympic athletes, shift workers, medical professionals, pilots, captains, truck drivers, emergency responders, etc.).

In any of the foregoing embodiments, data measured by the various functions described and included in the patch devices disclosed herein allow for measurement and estimation of the crucial parameters that influence the subject's circadian rhythm, namely, sleep onset time, sleep frequency, sleep duration, quality of sleep (presence of disturbances/wake events, etc.). Knowledge of sleep parameters allows for the programmed delivery of stimuli aimed at regulating sleep, improving sleep conditions, shifting sleep onset times according to desired schedules (e.g., time zone changes, etc.), and stabilizing sleep schedules in relation to activities for achieving peak cognitive and/or physical performance and disposition.

Figure 8:
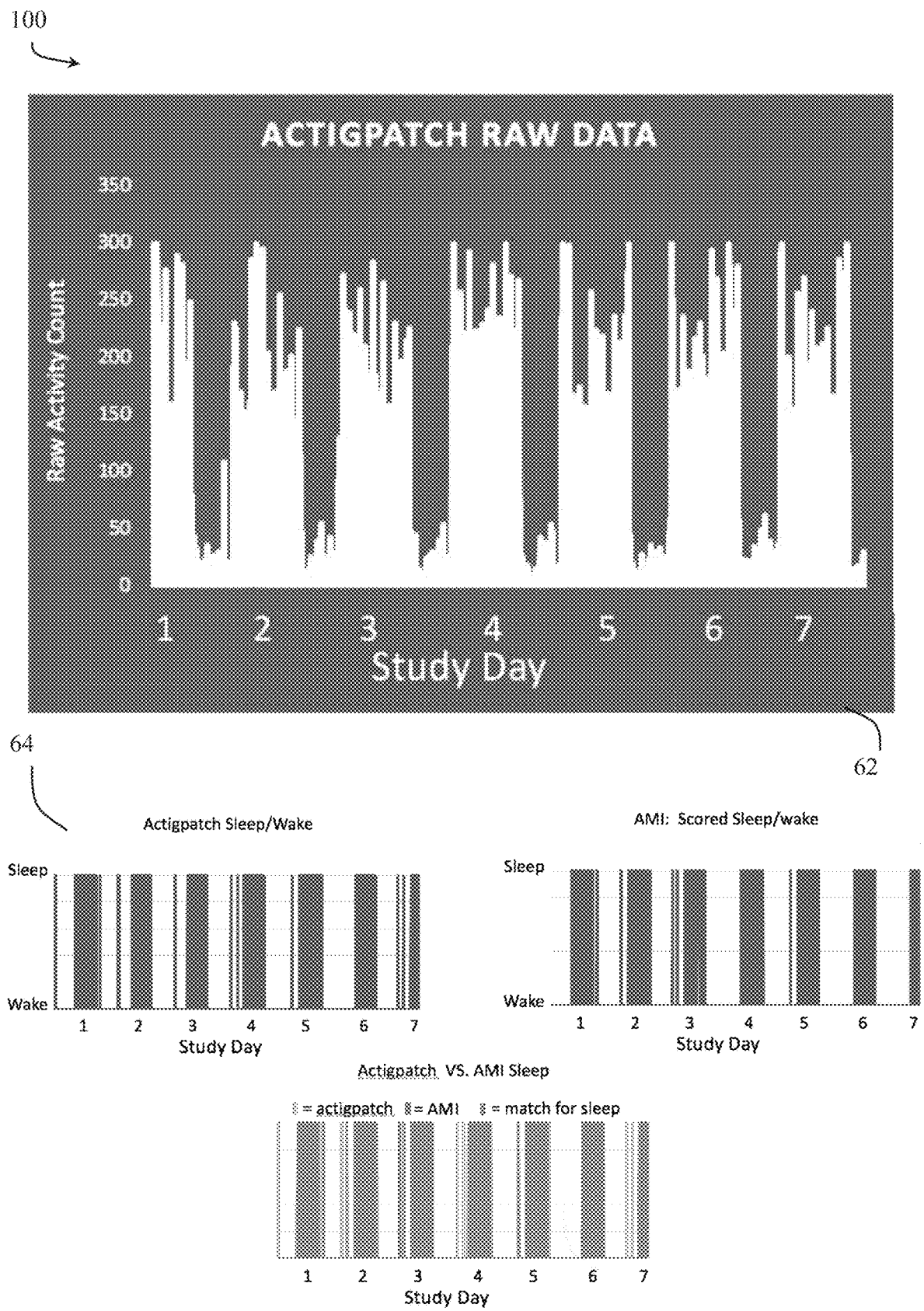
FIG. 8 illustrates activity data collected with a prototype activity measuring patch device placed on the subject's collar bone region in comparison with data collected with a wrist actigraph.

FIG. 8 depicts data collected by deployment of a patch and system 100 wherein data were collected during a 28-hours forced desynchrony laboratory study (FD). Activity/inactivity raw data [62] from patch sensors across seven earth days are presented. The graph at the top shows activity level on the y-axis and earth day on the x-axis. A clear pattern of high activity (wake) and low activity (sleep) are seen across study days. The smaller graphs show sleep/wake estimates [64] based from the raw data in the top graph. Actigpatch sleep/wake estimates (left), Ambulatory Monitoring, Inc. (AMI) actigraphy sleep/wake estimates (right) and the comparison of Actigpatch to AMI estimates (bottom) are displayed. These figures confirm high reliability in sleep/wake estimates between Actigpatch and AMI devices.

Figure 9:
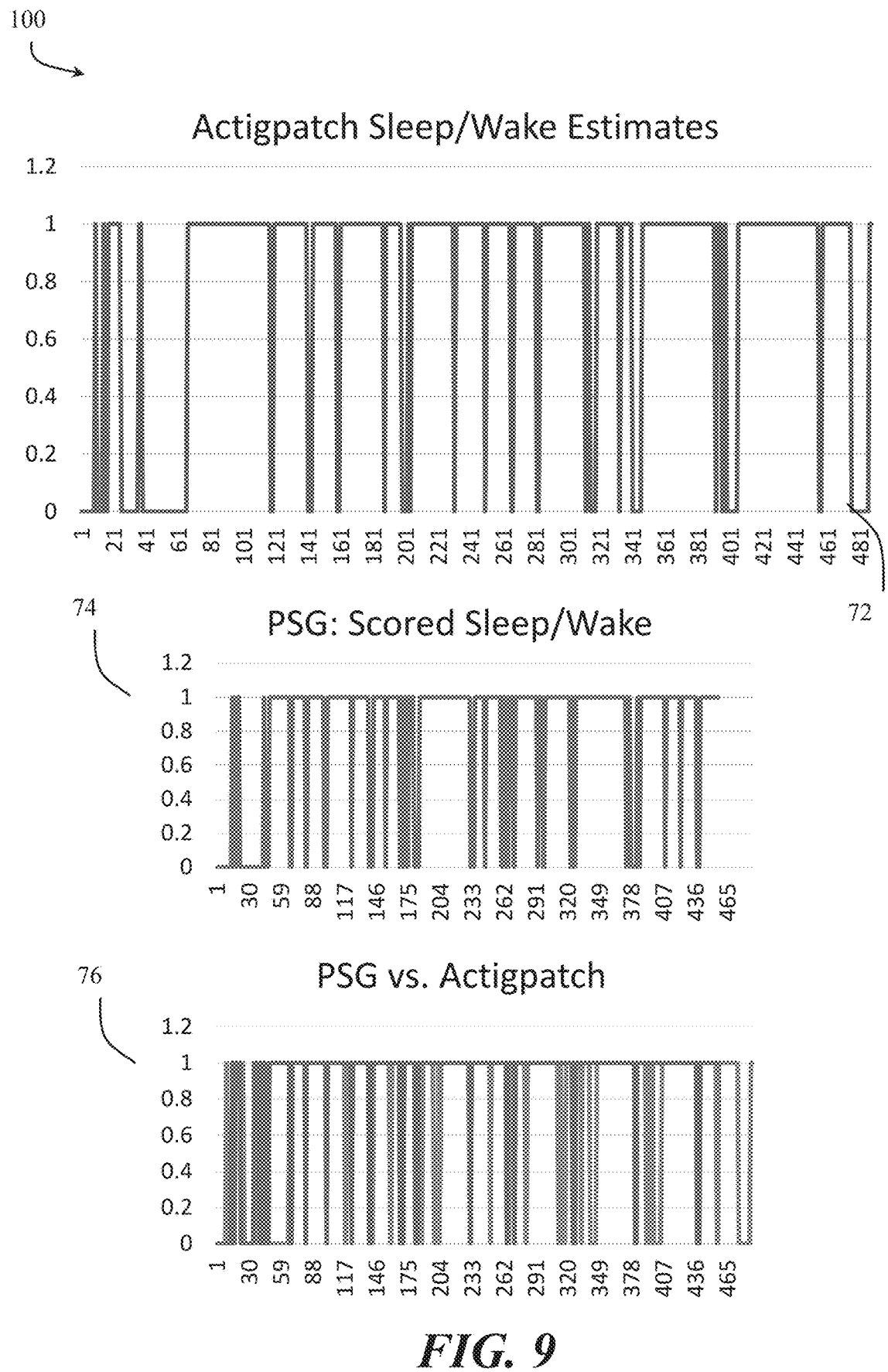
FIG. 9 illustrates sleep/wake estimates computed from data generated by the activity measuring patch device in comparison with the same estimates computed from the wrist actigraph's data.

FIG. 9 depicts data collected during a one night in-laboratory study measuring polysomnography (PSG) and activity/inactivity using the Actigpatch. Patch-based sleep/wake estimates across one night [62] are presented in the top graph. The subsequent graphs show polysomnographically (PSG) measured sleep/wake [74] scored according to Rechtschaffen and Kales (1968) criteria (top) and Actigpatch vs. PSG sleep/wake [76] (bottom). These data show reliability in sleep/wake estimates between Actigpatch and PSG.

Figure 10:
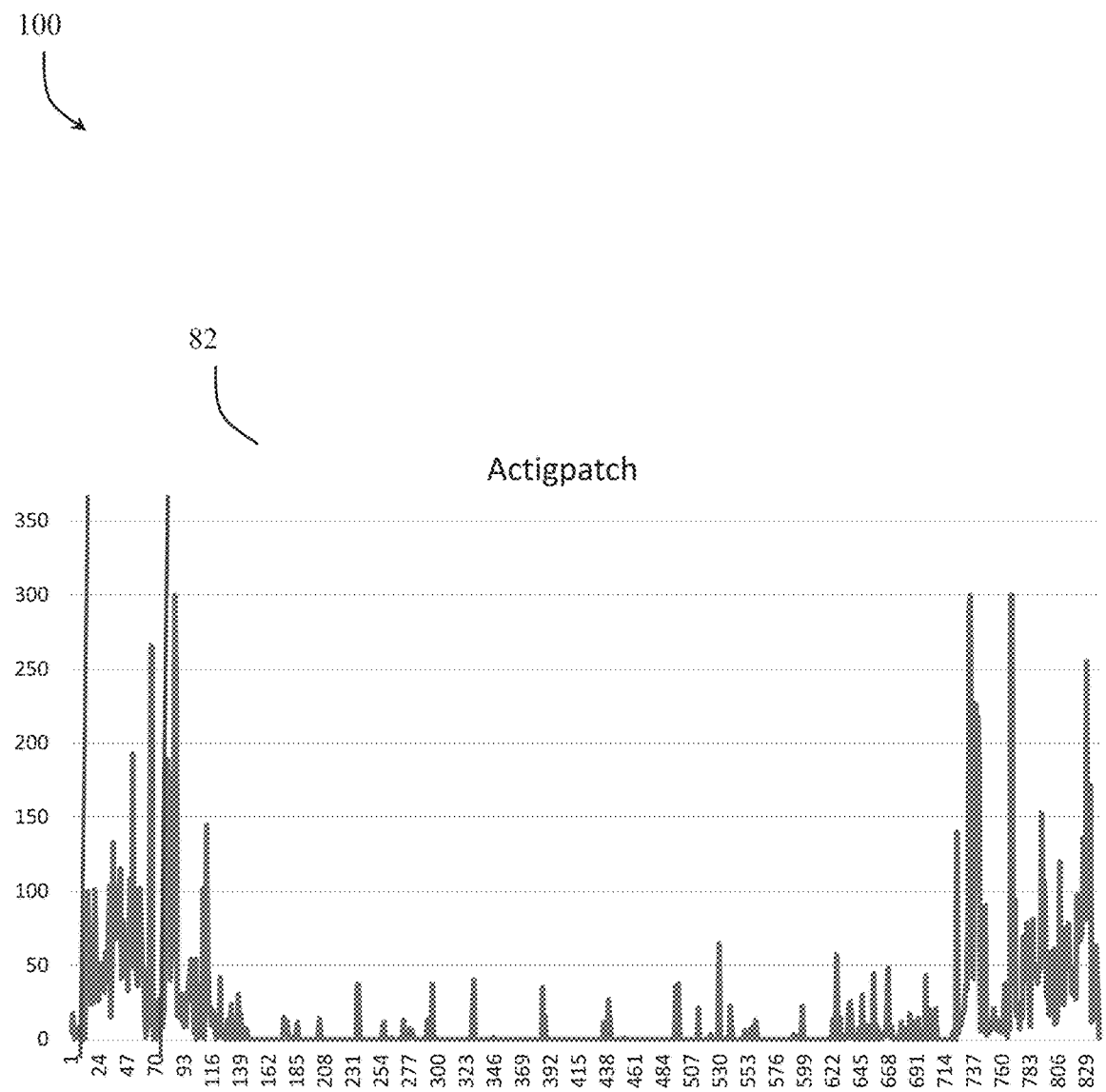
FIG. 10 illustrates one activity data record as produced by the activity measuring patch device spanning approximately 850 1-minute epochs.

FIG. 10 depicts data collected by Actigpatch showing activity level [82] (y-axis) across 24 hours (1 minute epochs; x-axis). Circadian phase was measured from salivary dim light melatonin onset (DLMO). A predictable time interval occurs between DLMO and sleep onset and this figure demonstrates that DLMO (circadian phase) can be estimated from sleep estimates derived from patch data collected from a subject.

FIGS. 11 through 16 illustrate an example embodiment or embodiments of the devices, systems and methods for estimating, modulating and improving the circadian phase and consciousness patterns of a subject (e.g., a human subject) by the dispensing of measured quantities of olfactory agents into an environment of the subject and the continuous monitoring and/or tracking of the subject's consciousness patterns, thereby aligning the subject's circadian biology to an external environment, improving the quality and duration of sleep, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Figure 11:
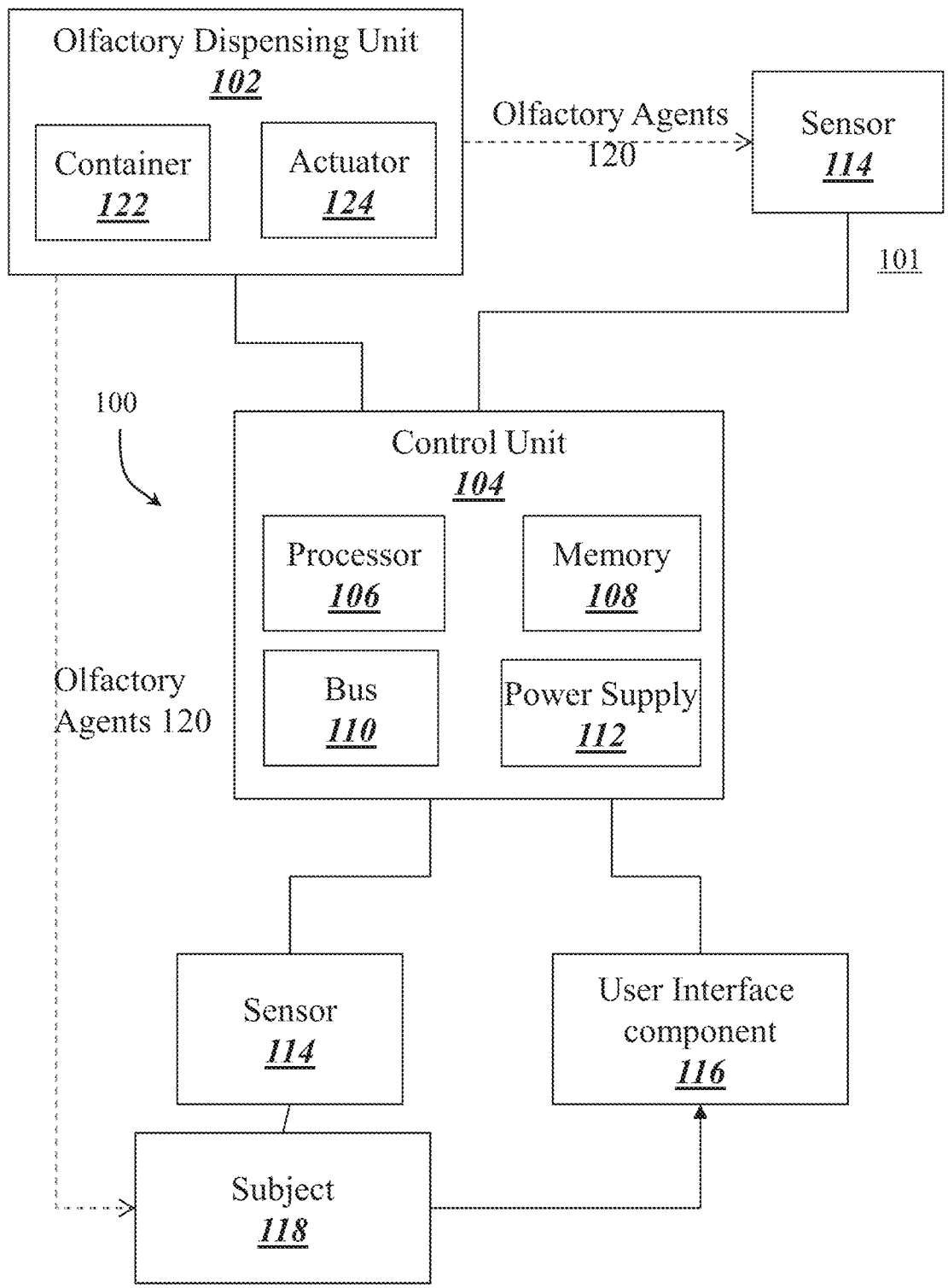
FIG. 11 illustrates an overview of the components and data flow of the system.

FIG. 11 depicts an overview of the components and data flow of the system 100. An aspect of the invention provides a system 100 for adjusting consciousness patterns/sleep/wake patterns and circadian states of one or more subjects 118 based on tracking and estimating subject 118 responses, the system comprising a control unit 104 to control an olfactory dispensing unit 102 and being operative to dispense olfactory agents 120 including at least one of: a fragrance, odor, scent, and olfactory stimuli, which are dispensed during a programmed or specified time/circadian phase relative to sleep onset/offset in order to facilitate, enhance, and consolidate sleep or enhance mood and alertness in a subject. In certain embodiments, the subject 118 is a human (e.g., a shift worker or a member of the military), but may be another organism that has suitably responsive olfactory cells.

In general, the control unit 104 applies an olfactory formulation to facilitate or enhance sleep or the timing of sleep or enhance alertness/performance and mood. The control unit 104 controls a set of olfactory agents 120 including at least one of odors, scents, fragrances and olfactory stimuli to set a prescribed olfactory supplement and/or schedule. In an embodiment of the system 100, the control unit 104, olfactory dispensing unit 102 and the olfactory agents 120 are assembled in a kit or container, which is portable.

The control unit 104 in various embodiments receives a biofeedback signal or data indicative of one or more subjects' 118 consciousness patterns, defined as either sleep patterns, patterns detected from a subject 118 while awake, or a combination of both, and determines the formulation in accordance with that signal or data, to achieve a desired response in the subject 118 (e.g., shifting of the subject's timing of sleep, reducing sleep onset latency, enhancing sleep consolidation, reducing variability in sleep patterns, etc.). The control unit 104 of the system 100 allows for timed (e.g., both time of day, time relative to sleep, and/or circadian phase) delivery of precisely measured quantities of olfactory agents 120 that alter or otherwise modulate circadian rhythms and consciousness patterns of subjects 118, wherein the control unit 104 comprises a real-time clock or timing device for providing precise times to perform functions and timestamps for the measurements taken by the system 100.

This system 100 is located in a designated area (e.g., bedroom, bathroom, playroom, office, car, gym, plane, ship, etc.) defined as the environment 101 of the one or more subjects 118.

Figure 12:
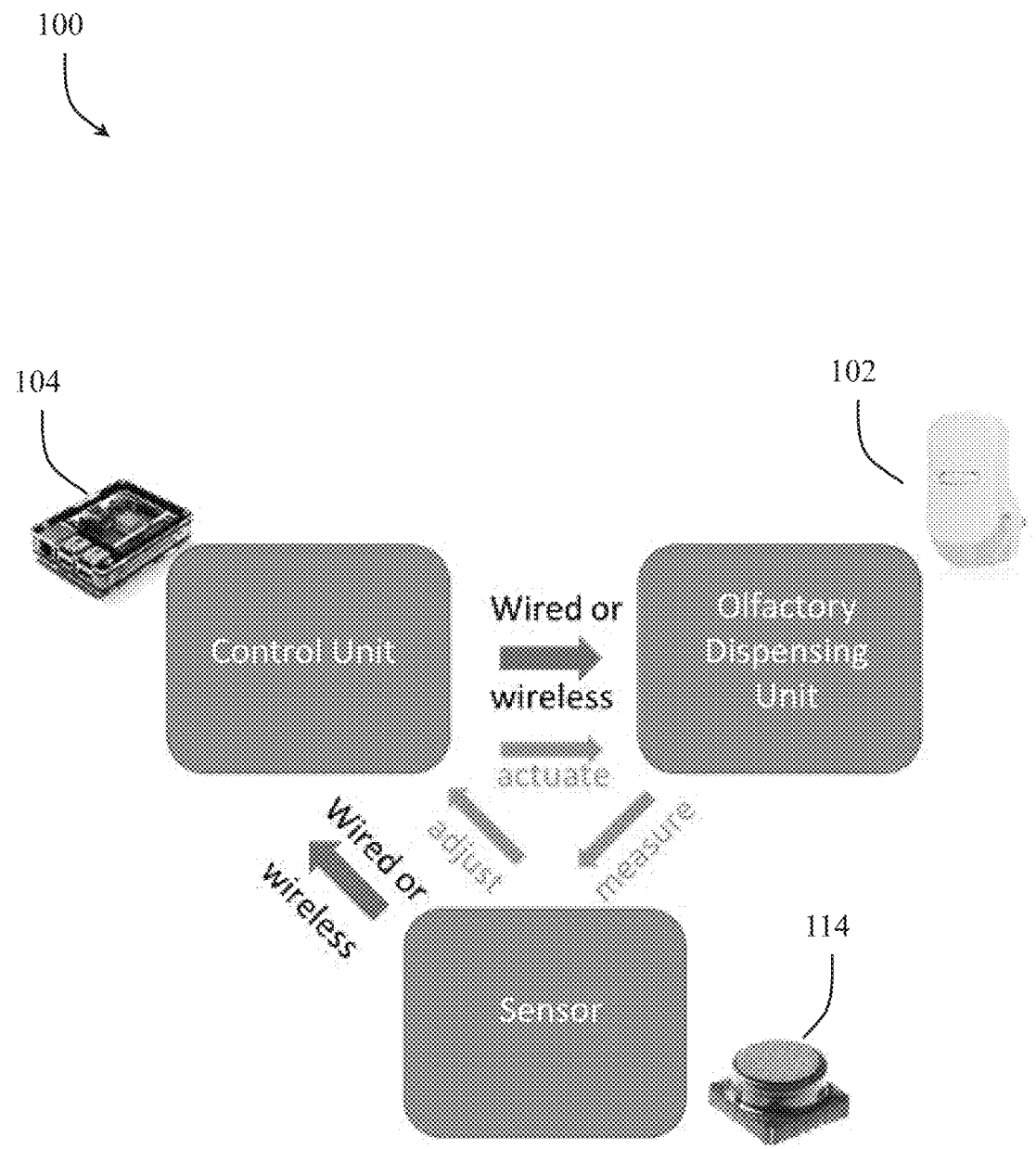
FIG. 12 illustrates the flow of data and electronic communication for used components for embodiments of the system.

The method of olfactory agent 120 delivery is not crucial for the operation of the system 100, however, ability to control the timing (when) and amounts (how much) of olfactory agent 120 delivery is central to the system's 100 operation. FIG. 12 illustrates the flow of data and electronic communication for commonly used components for embodiments of the system. The olfactory agent 120 delivery can be accomplished via the use of electrical heating of odor oils and other liquids to cause evaporation (a similar operative mechanism to commercial scented oil heating devices e.g., Glade® Plug-Ins®), via ultrasonic nebulizers, via air-stream atomizers, or via the use of volatile substances. In the case of electrical heating, the heater must be actuated by the control unit 104 at specific times dictated by the formulations; for the ultrasonic nebulizer, the vibrating (piezo) element must be actuated by the control unit 104; for the air stream nebulizers, an air pump or other air-stream generating device must be actuated by the control unit 104; for volatile substances, the compartment containing the substance must be opened and closed by the control unit 104, allowing or not allowing the vapors to propagate out of the device and into the air. A fan (not shown), for circulating air through the device or the system 100 may be added.

Each olfactory formulation consists of a list of times and desired olfactory stimulus (odor, aroma) concentrations, in the form of olfactory agents 120, at each time. The critical quantity that dictates the system's 100 operation and quantifies the size of the olfactory stimulus is the amount of olfactory agents 120 absorbed by the subject 118 over a certain period (i.e. concentration multiplied by exposure time). Insofar as the formulation is concerned, the stimulus and olfactory agent 120 concentrations can be measured in absolute units (e.g., μg of odor per liter of air) or in "empirical" units (e.g., the concentration that results when the olfactory dispensing unit 102 is actuated for X units of time in a room of Y cubic meters of volume). Once the characteristics of the dispenser are known, these two measurement methods are completely equivalent.

The control unit 104 actuates the olfactory dispensing unit 102 as a function of time, according to the formulation. The control unit contains a clock that allows it to keep time for precise function initiation and timestamping data, and memory 108 (comprising volatile and non-volatile memory for storing program code and measured data) to store the formulation. Additionally, the control unit's 104 memory 108 may store data from sensors 114 and other devices that allow it to compute relevant parameters and adjust the formulation in real-time. The control unit uses consciousness patterns data of each of the one more subjects to optimize a formulation of the olfactory agents in real-time to provide cues to achieve a stimuli response in each of the one or more subjects. Optimization occurs when the measured stimuli response of the one or more subjects matches the data provided by the formulation and user input including maintaining specific concentrations of olfactory agents in the environment 101 and absorbed by the one or more subjects 118. The stimuli response comprises one or more actions selected from the group consisting of shifting of timing of sleep, adjusting circadian phase, enhancing alertness, enhancing performance, reducing sleep onset latency, enhancing sleep consolidation and reducing variability in sleep patterns and adjusting mood. When internal circadian time is aligned to the external environment, physiological and behavioral processes are enhanced (e.g., sleep, cognitive and physical performance, alertness, metabolism, and gastrointestinal function perform more efficiently). Alertness and performance are defined and measured by comparison of patterns of activity for persons awake with historic activity with respect to timing to perform known tasks and accuracy in performance. Enhancing sleep consolidation means reducing in duration or removing discontinuities in sleep or lengthening the duration of uninterrupted sleep or both. Adjusting mood means delivering olfactory agents 120 known to cause physiological changes to observed phenomena identified in the art as moods or triggering behavior in a subject using pre-conditioning of the subject to initiate or cease moods based on prior associations and administrations of olfactory agents 120. Several stimuli have direct and indirect influence on circadian rhythms, sleep, and performance (e.g., light, melatonin and caffeine) and the appropriately timed (e.g., circadian phase, time relative to sleep or wake, and time relative to scheduled performance) administration of such stimuli, for example, can shift circadian biology to better match the external environment, thereby enhancing performance, alertness, mood, sleep, etc. of a subject. Different formulations that promote different stimuli responses may be stored in the memory 108 of the control unit, input by the user, or determined by analysis of sensor 114 data processed by the processor 106 of the control unit 104. The control unit 104 works in conjunction with a user interface 116 that may be a component of the control unit 104 or a separate component, wherein the users can modify the system's 110 parameters, tweak formulations, etc. This user interface 116 can be provided via wired (USB, UART, etc.) or wireless technologies (Bluetooth, Bluetooth low energy (BLE), Zigbee, Wi-Fi, infrared, near field communication, etc.) or via a display and buttons on the control unit 104 itself. The control unit 104 can be a dedicated hardware device, built solely for the purpose of controlling this system 100, or a general purpose device, such as a smart-phone or a tablet computer running dedicated software that controls the system. The system 100 can include or comprise software that tracks sleep history information of the one or more subjects, then sets a sleep-and-wake schedule for the one or more subjects and designates specific olfactory agents assigned to activity events selected from the group consisting of bedtime, risetime, nap time, awake time and combinations thereof. The olfactory agents can be automatically dispensed at specific times of day to facilitate at least one action selected from the group consisting of sleep, wake, increased alertness, and relaxation. The system uses algorithms to avoid habituation to olfactory agents relative to onset of activity events. In addition to the control unit 104, the system 100 comprises sensors 114, and the olfactory dispensing unit 102, which comprises one or more containers 122 that store the olfactory agents 120, and actuators 124 that deliver the olfactory agents 120 into the environment 101. Different system embodiments can be contemplated. Various methods of actuation are possible.

The system 100 may comprise one or more sensors 114, that collect data and measurements associated with the subject 118, the environment 101 of the subject 118, or both. In some cases, it may be possible to directly measure the concentration of olfactory stimulant or olfactory agents 120 in the air. Technologies for measuring aromas are a subject of current active development. Sensors 114 for certain specific gases and volatile organic compounds (VOC) may be suitable for estimating the concentration of certain aromas in the air. Certain novel sensors 114 that map aromas to images (e.g., the Aroma Bit sensor) may be suitable for these applications. In such cases when aroma concentrations can be measured or estimated directly, the system 100 can be operated as a "servo" to precisely control the quantity of olfactory agent 120 present in the air at any given time. If measurement of such concentration is not possible, then the system 100 operates exclusively as an actuator, and its output (or intensity) must be configured according to the ambient environment 101 in which it is used for achieving the desired concentrations. Additionally, if such direct measurements of the olfactory agent's 120 concentration are impossible, the system's 100 operation may also be precisely controlled as a "servo" by measurements of circadian outcomes and application of machine learning techniques to indirectly infer adequate concentrations. In certain embodiments, the functions of the one or more sensors 114 quantify the subject's 120 sleep and circadian system including monitoring a subject's rest and activity cycles via actigraphy (movement measurement with an accelerometer), recording movements and activity, measuring environmental light exposure with photodiodes or other light sensitive devices, collecting and monitoring polysomnographic data (e.g., electroencephalogram, electrooculogram, and electromyogram, and electrocardiogram) via electrical pads that contact the subject's skin, measuring the subject's skin temperature, measuring the subject's blood oxygen saturation levels, transdermal sensing, such as pulse/blood oximetry and analysis of sweat and other skin secretions of the subject (e.g., for hormones that may contain information relevant for the assessment and manipulation of circadian rhythms and sleep patterns), and/or measuring sleep onset time and duration, and other measurements of motion and sleep readily apparent to a person of ordinary skill in the art. The system 100 can use this information to improve the formulation in real time. The sensors 114 may be separate from the control unit 104, however in some embodiments the control unit 104 may have components that act as one or more sensor 114. In certain embodiments, sensors 114 include or comprise patches that are worn on the skin of one or more subjects 118 and related components for determining and/or estimating and tracking subjects' 118 consciousness patterns (wake/sleep patterns) and circadian state, and other data related to shifting and/or aligning the subject's circadian state to external schedules based on measured data and smart algorithms. In certain embodiments, sensors 114 may include or comprise a communications interface, wired or wireless, that allows for data to be transferred from the sensors 114 to the control unit 104, a computer, tablet or phone, or other device incorporating a real-time clock capable of providing timestamps for the measurements from sensors 114.

Figure 13:
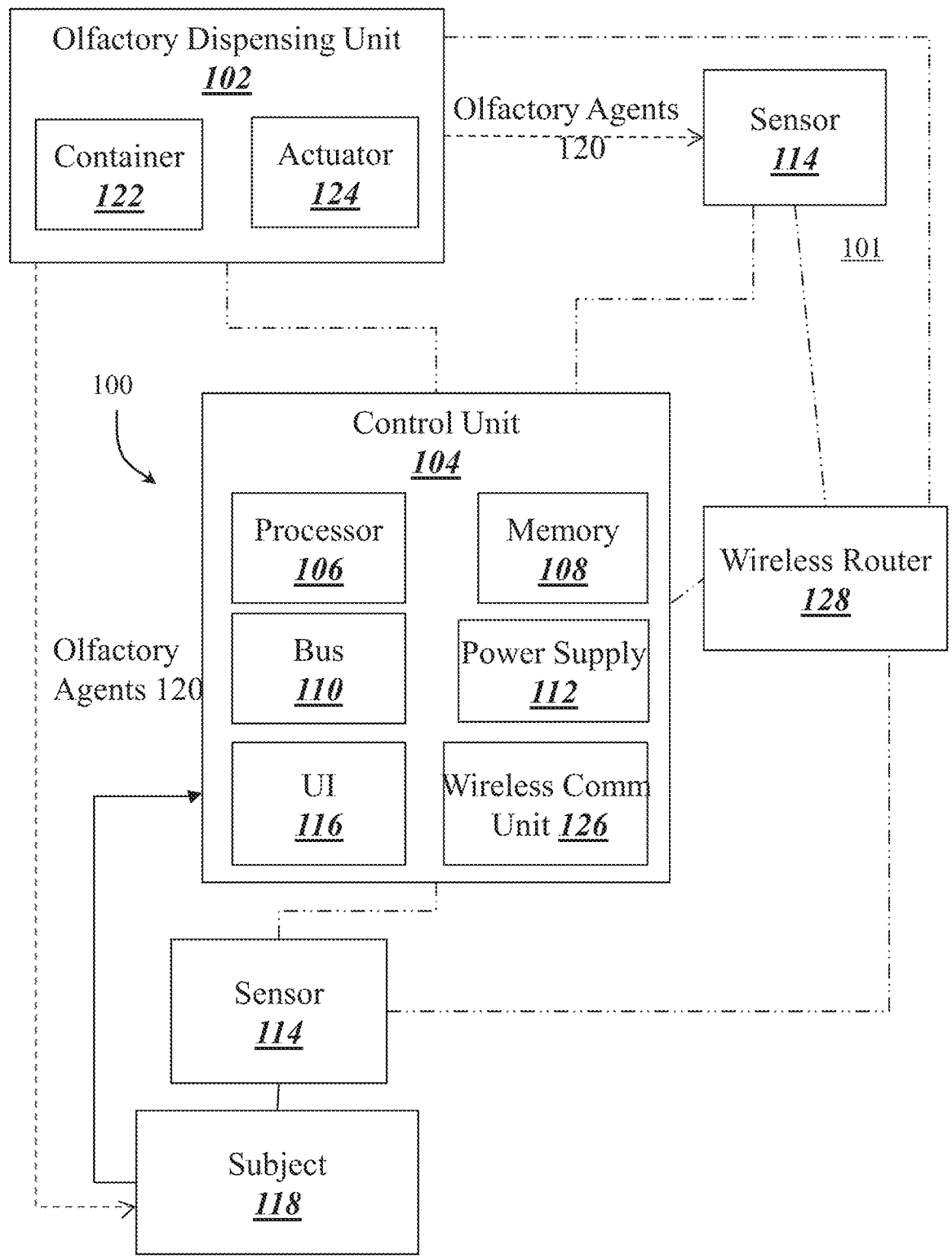
FIG. 13 illustrates an embodiment where the system is configured to use wireless electronic communication.

The physical layout of system 100 components also can vary without consequence to the system's 100 operation. In one alternative embodiment, the control unit 104 is physically separated from the olfactory dispensing unit 102 that stores and dispenses the olfactory agents 120. In such an embodiment, more than one olfactory dispensing unit 102 can be controlled by one control unit 104. The olfactory dispensing units 102 are connected to the control unit 104 via wired or wireless technologies, including Bluetooth, Bluetooth low energy (BLE), Zigbee, Wi-Fi, infrared, near field communication, etc. Referring to FIG. 13, the system is configured to use wireless electronic communication. The control unit 104 provides a user interface 116 wherein the users can modify the system's 100 parameters, tweak formulations, etc. This interface can be provided via wireless technologies (Bluetooth, Bluetooth low energy (BLE), Zigbee, Wi-Fi, infrared, near field communication, etc.) or via a display and buttons on the control unit itself. The control unit 104 can be a dedicated hardware device, built solely for the purpose of controlling this system, or a general purpose device, such as a smart-phone or a tablet computer running dedicated software that controls the system 100. The control unit 104 can contain a wireless communication unit 126 that allows the control unit 104 to communicate electronically using wireless technologies, including the use of devices including wireless routers 128 that enable the control unit 104 to remotely communicate with the olfactory dispensing units 102 and sensors 114 to send commands and receive data.

Figure 14:
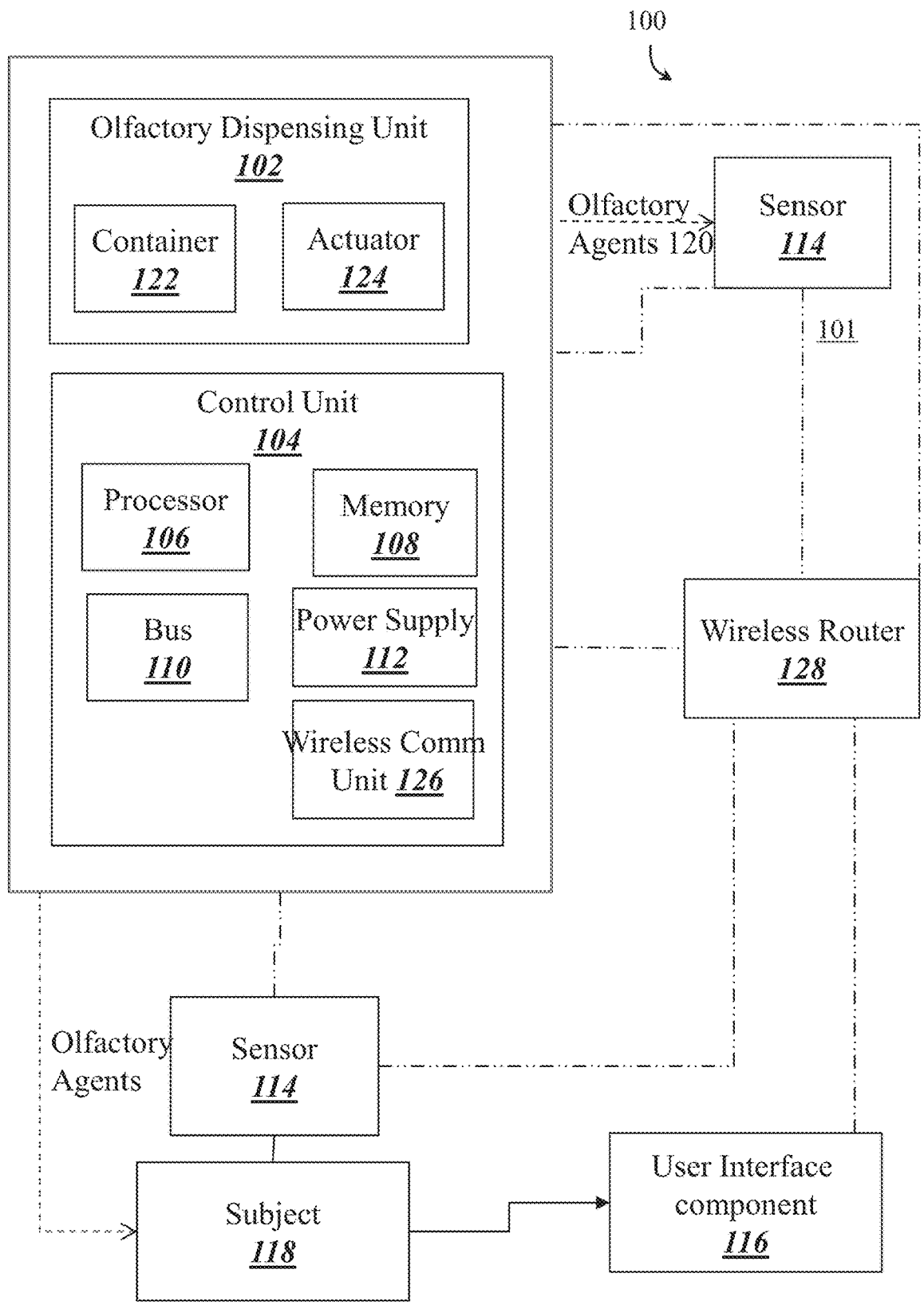
FIG. 14 illustrates an embodiment of the system wherein the control unit and olfactory dispensing unit operate within a single device.

In an alternate embodiment, the control unit 104, and olfactory dispensing unit 102 with container 122 and actuator 124 reside in the same physical device. FIG. 14 illustrates an embodiment of the system wherein the control unit 104 and olfactory dispensing unit 102 operate within a single device. The formulation is stored in the control unit's 104 memory 108, and the control unit 102 then controls the dispensing of olfactory agents 120 as required.

Figure 15:
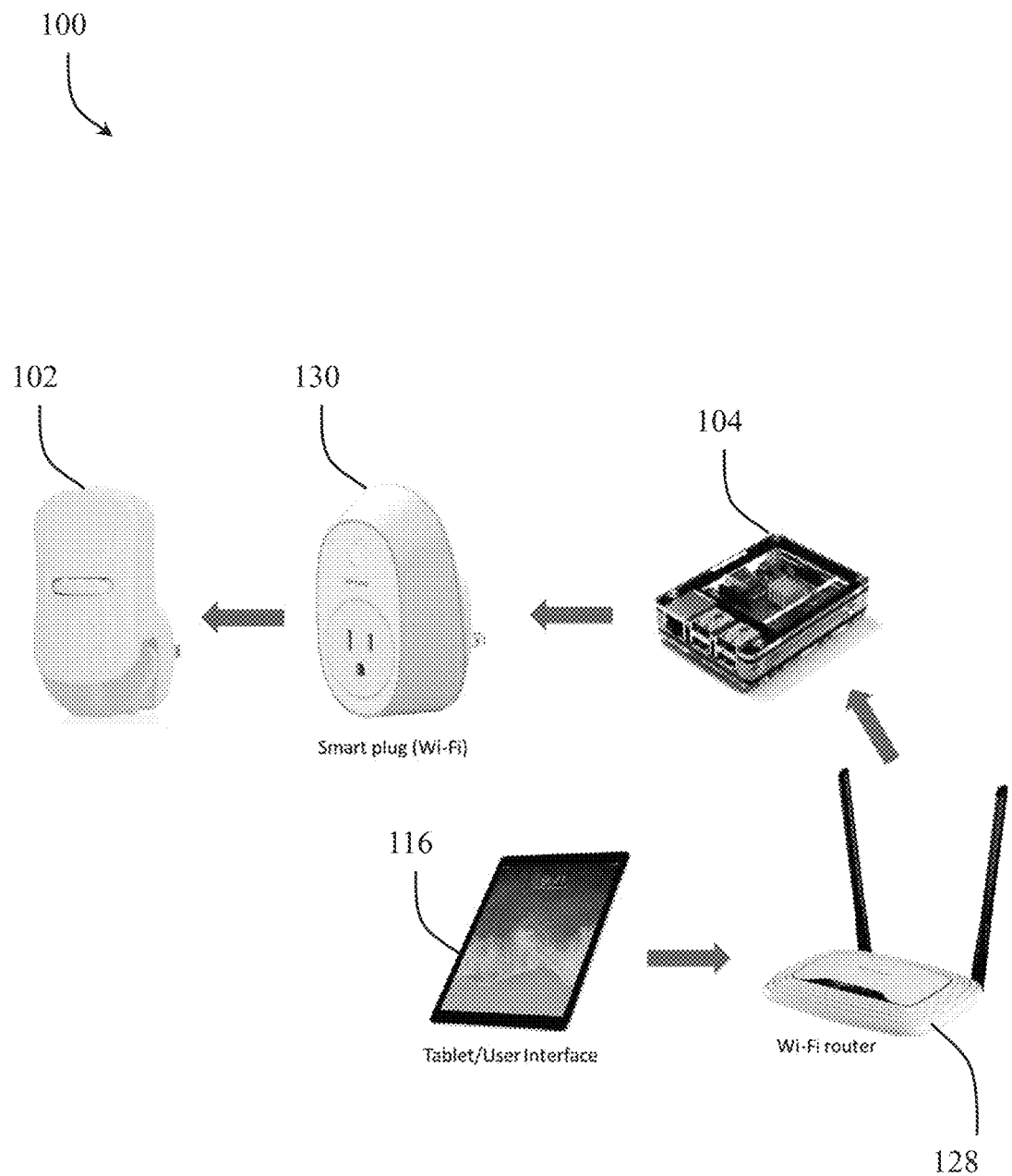
FIG. 15 depicts an embodiment of the system wherein the control unit and dispensing unit operate as a smart plug.

FIG. 15 depicts an alternative embodiment of the system wherein the control unit and dispensing unit operate as components of a smart plug. In accordance with an alternative example embodiment of the present invention, this smart device can be used to improve the sleep of babies and infants, by providing olfactory cues circa bedtime. In its simplest form, this alternative embodiment comprises a single physical unit, similar in form to a Glade® Plug-In® device, but rather than simply containing scented oil warming components activated by insertion into an outlet, the smart plug device contains the control unit 104, the olfactory dispensing unit 102 complete with the one or more actuators 124 and 122 one or more containers of olfactory agents 120, and wireless transceiver 126 in the same package. The control unit 104 can be accessed and configured via Bluetooth Low Energy or other similar technology. Configuration comprises simply of inputting the desired bedtime, duration and intensity of dispensing, and dimensions of the subjects' 118 environment 101 which in this embodiment would include or comprise the baby's bedroom. With this information, the system 100 pre odorizes the baby's bedroom with olfactory agents 120 every day at bedtime using the control units 104 ability to perform actions as a function of time, and thereby pre-conditions the baby to want to sleep at that time.

Figure 16:
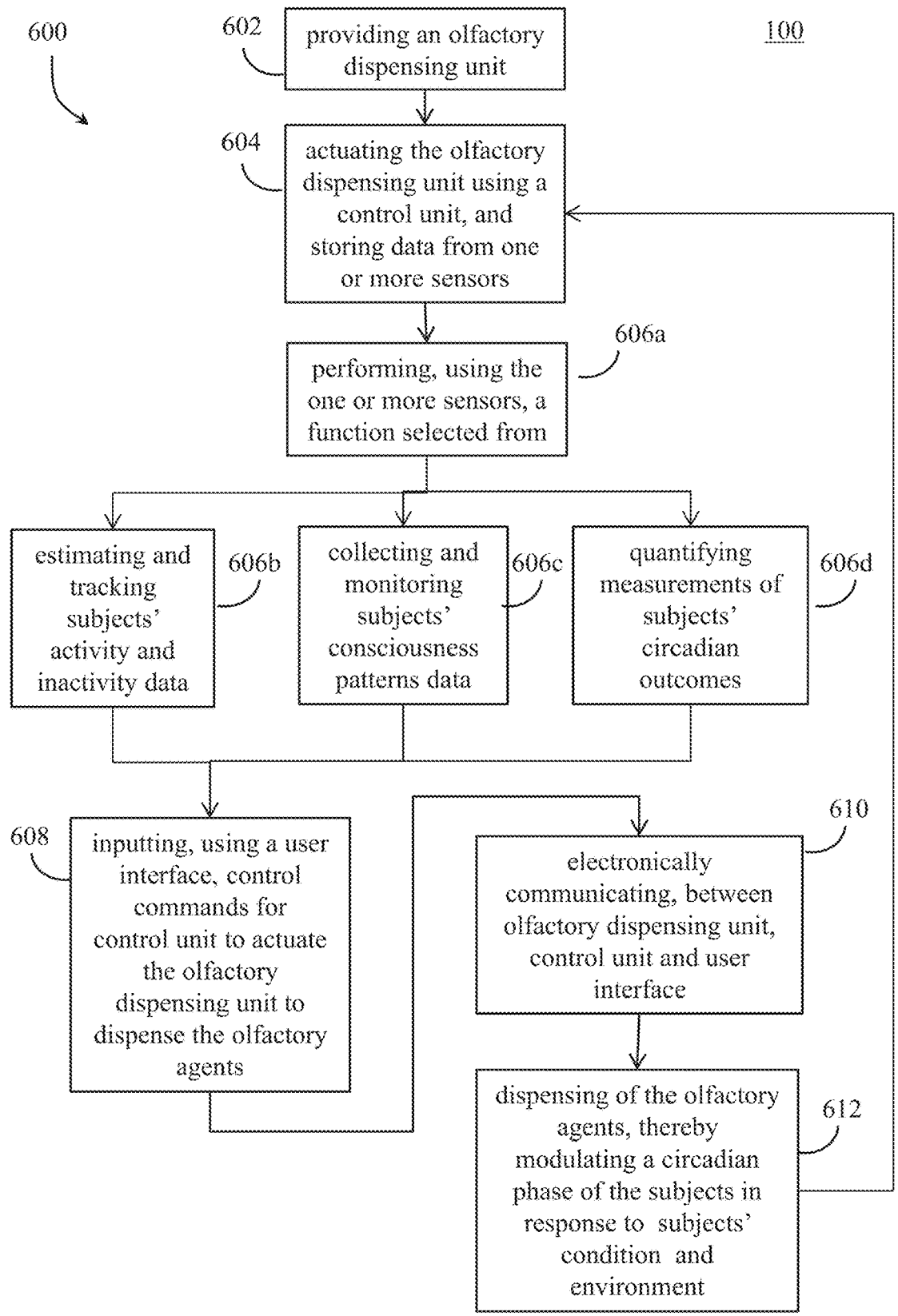
FIG. 16 depicts an illustrative flowchart showing the method for carrying out the operation of the system.

FIG. 16 depicts an exemplary flowchart showing the method 600 for carrying out the operation of the system 100 to provide adjustment of consciousness patterns and circadian states to one or more subjects 118 through the monitoring and use of olfactory agents 120 supplied into the environment 101 of the one or more subjects 118. At step 602, a user, who may also be one of the subjects 118, provides the olfactory dispensing unit 102 into the desired environment 101 of the one or more subjects 118, by performing actions such as, initial set up of the olfactory dispensing unit 102, unpacking the olfactory dispensing unit 102 from a kit, and supplying power to the olfactory dispensing unit 102 by inserting a power supply such as a battery (rechargeable or not) or inserting the olfactory dispensing unit 102 into an electrical outlet found in the desired environment 101 of the one or more subjects 118.

At step 604, a user (e.g., a subject) activates the control unit, by performing actions such as, initial set up of the control unit 104, unpacking control unit 102 from a kit, supplying power to the control unit 104 by inserting a power supply 112 such as a battery (rechargeable or not) or connecting the control unit 104 to an electrical outlet, then powering on the control unit 104 and actuating the olfactory dispensing unit 102 using a control unit 104, and storing data in memory 108 gathered from one or more sensors 114 using a processor 106, that are activated by the control unit 104.

At step 606a, the one or more sensors 114 may be used to perform one or more of several functions that use data gathered from the sensors 114 and the control unit 104 including: estimating tracking and predicting 606b activity and inactivity data for one or more subjects 118, collecting and monitoring 606c consciousness patterns data for one or more subjects 118, and quantifying measurements of circadian outcomes 606d for one or more subjects 118.

At step 608, the user inputs control commands using the user interface 116, which use the control unit 104 to actuate the olfactory dispensing unit 102 to dispense the olfactory agents 120 into the environment 101 of the one or more subjects 118, according to a specific formulation and parameters selected by the user and stored in the memory 108 of the control unit 104 which performs functions related thereto using the processor 106.

At step 610, the control unit 104 and the olfactory dispensing unit electronically communicate with each other to control further actuation and dispensing of olfactory agents 120 to follow the formulation required by the control unit 104. The control unit and the user interface electronically communicate to provide the user with information related to the dispensing of olfactory agents 120 and data related to the environment 101 and the one or more subjects 118 collected from the sensors 114 or stored in the control unit 104 memory 108.

At step 612, the control unit 104 continues to follow the specific formulation as a function of time, actuating the olfactory dispensing unit to continue dispensing various amounts of the olfactory agents 102, thereby modulating sleep/wake and/or a circadian phase of the one or more subjects 118, based on data related to the environment 101 and the one or more subjects 118 collected from the sensors 114 or stored in the control unit 104 memory 108, where adjustments to timing and amount of olfactory agents 120 dispensed are made in response to a condition of the one or more subjects 118 and an environment 101 of the one or more subjects 118 as measured by the sensors 114 in real time. This process of adjusted dispensing of olfactory agents 120 based on sensor 114 measurements is iteratively repeated to continually adjust the stimulus provided to the subjects 118, modulating a circadian phase of the one or more subjects 118 for the duration specified by the control unit 104. The control unit 104 may end dispensing of olfactory agents 120 or introduce other olfactory agents 120 to signal the end of a particular administration, consciousness pattern, or circadian phase of the one or more subjects 118, for example when the sleeping period has ended.

EXAMPLES

Example 1: Modulating Circadian Phase

The devices, patches, systems and methods disclosed herein modulate the circadian phase and/or sleep/wake of a subject in response to the subject's environment. Such devices, patches, systems and methods include or comprise a step of determining the subject's activity counts when the subject is awake or asleep. Based on the subject's pattern of sleep/wake the beginning and end of biological night would then be determined. This estimate of early biological night and late biological night allows for the administration of one or more interventions, for example by controlling or administering light, stimuli and/or agents, capable of shifting the subject's circadian system. For example, melatonin can be administered to a subject in the early biological night to advance the subject's circadian rhythms and very late biological night to delay the subject's circadian rhythms. Similarly, light can be used in the early biological night to delay phase and late biological night to advance the subject's circadian phase. The particular intervention is determined based on estimated circadian phase during the biological night/day and desired time of performance. For example, if a subject has one week to phase advance to European time from New York, USA time, the devices, patches and systems disclosed herein would use the current sleep/wake schedule of that subject to determine when late biological night is and administer a specific light recipe (e.g., as described in U.S. Provisional Application No. 62/511,692, entitled "Smart light system for circadian system stabilization and conditioning for mission-critical applications," and/or International Publication Number WO 2018/218241, entitled "Lighting System for Circadian Control and Enhanced Performance," the entire contents of which are incorporated by reference herein) during that time and then administer melatonin to the subject during the early biological night. Similarly, in certain aspects, the devices, patches and systems disclosed herein can administer, for example, caffeine to a subject in advance of critical performance times.

Example 2: 28-Hours Forced Desynchrony Laboratory Results

Through significant experimentation, the inventors were able to successfully collect data during a 28-hours forced desynchrony laboratory study (FD). Activity/inactivity data across seven earth days are presented in FIG. 8. These data are from a healthy adolescent-aged participant. The graph on the top presents raw actigraphy data collected by a patch ("Actigpatch") that shows activity level on the y-axis and earth day on the x-axis. A clear pattern of high activity (wake) and low activity (sleep) are seen across study days. The graphs in the middle of the figure show sleep/wake estimates based on the raw data in the top graph. Actigpatch sleep/wake estimates (left), Ambulatory Monitoring, Inc. (AMI) actigraphy sleep/wake estimates (right) and the comparison of Actigpatch to AMI estimates are displayed on the bottom graph. These figures confirm high reliability in sleep/wake estimates between Actigpatch and AMI devices.

Example 3: Overnight Laboratory Results

Through significant experimentation, the inventors were able to successfully collect data during a one night in-laboratory study measuring polysomnography (PSG) and activity/inactivity using the Actigpatch. Data are from a healthy 32 year old male. Patch-based sleep/wake estimates across one night are presented in the graph on the top of FIG. 9. The graph in the middle of that figure shows polysomnographically (PSG) measured sleep/wake scored for the same subject and study according to Rechtschaffen and Kales (1968) criteria, and Actigpatch vs. PSG sleep/wake are compared in the graph at the bottom of FIG. 9. These data show reliability in sleep/wake estimates between Actigpatch and PSG (a "gold standard" by which sleep/wake patterns are measured).

Example 4: Circadian Phase Laboratory Results

Through significant experimentation, the inventors were able to successfully collect data presented in FIG. 10 that originates from the first in-laboratory night. These data are from a healthy adolescent. Activity level (y-axis) is plotted across 24 hours (1 minute epochs; x-axis). Circadian phase was measured from salivary dim light melatonin onset (DLMO; a "gold standard" by which circadian phases are measured). The first vertical indicator line shows measured circadian phase and the second vertical indicator line shows sleep onset. A predictable time interval occurs between DLMO and sleep onset and this figure demonstrates that DLMO (circadian phase) can be estimated from sleep estimates using data collected from patches.

As used herein, a "subject" means a human or animal whose circadian state (e.g., sleep onset) is modulated by the inventions disclosed herein. In certain embodiments, the subject is also the user of the inventions disclosed herein. Conversely, in other embodiments, the subject is not the user, but rather the user may be, for example, an administrative user of the system that is responsible for modulating the circadian states of one or more subjects (e.g., a group of military subjects under the command of the users). In certain embodiments, the subject is a mammal (e.g., a primate or a human). The subject may be an infant, a toddler, a child, a young adult, an adult or a geriatric. In certain aspects, the subject is a member of the military.

As used herein, the term "agent" broadly refers to any compound or molecule (e.g., a small molecule organic compound) that is delivered to a subject in accordance with the inventions disclosed herein. In certain aspects, the agents modulate circadian biology of the subject. In certain aspects, the agents are used to modulate a subject's circadian biology or circadian rhythm (e.g., to align such subject's circadian biology or rhythm to an external environment). In certain embodiments, the agents include or comprise one or more central nervous system stimulants (e.g., modafinil, methylphenidate, and/or methylxanthines such as caffeine,). In certain embodiments, the agents include or comprise one or more central nervous system depressants (e.g., melatonin, opioids, hypnotics, benzodiazepines, barbiturate and/or antihistamines). In some aspects, the agent includes modafinil. In some aspects, the agent includes one or more sedatives (e.g., sleeping pills, pain medications and combinations thereof). In some embodiments, the agent includes a circadian phase shifting agent (e.g., melatonin, hormones, light, and combinations thereof). In still other embodiments, the agents include or comprise one or more hormones. In certain embodiments, the agents are topically administered. In certain embodiments, the agents are absorbed transdermally.

As used herein, the terms "modulating" or "modulation" mean to affect, alter or otherwise adjust the circadian biology or circadian phase of a subject. In certain contexts, modulating the circadian biology or circadian phase of a subject means to correct, adjust or otherwise change the subject's circadian biology or circadian phase consistent with such subject's current or anticipated environment. For example, modulating a subject's circadian phase to better coincide or align with a subject's anticipated travel to a new time zone.

As used herein, references to a subject's "circadian phase," "circadian rhythm" or "circadian biology" generally refer to such subject's internal timing of the circadian clock and outputs of the circadian clock housed in the mammalian suprachiasmatic nucleus of the anterior hypothalamus. For example, the devices, patches, systems and methods disclosed herein may, in certain aspects, collect data from a subject and/or the subject's environment, and use such data to inform the degree to which such subject's circadian phase will be modulated, shifted or otherwise corrected in accordance with the present inventions.

While certain compositions, devices and methods of the present invention have been described with specificity in accordance with certain embodiments, the following examples serve only to illustrate the methods and compositions of the invention and are not intended to limit the same.

The articles "a" and "an" as used herein in the specification and in the claims, unless clearly indicated to the contrary, should be understood to include or comprise the plural referents. Claims or descriptions that include or comprise "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or the entire group members are present in, employed in or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

What is claimed is:

1. A patch for determining and tracking one or more activity/inactivity patterns, polysomnographic patterns and circadian states of a subject, the patch comprising:
    a microcontroller, volatile and non-volatile memory, a communications interface, and a battery;
    one or more electrical pads configured to contact skin of the subject and collect and monitor polysomnographic data selected from the group consisting of brainwave data, eye movement data and muscle tone data, consciousness patterns, and activity/inactivity patterns measuring rest and activity cycles via actigraphy for the subject;
    wherein the microcontroller is configured to estimate or determine, a circadian phase of the subject based on the collected and monitored polysomnographic data;
    one or more actuating devices configured for controlled transdermal delivery of one or more agents that alter circadian rhythm of the subject through at least one nozzle based on the estimated or determined circadian phase;
    wherein the delivery of the one or more agents is configured to modulate one or more of: the circadian phase and consciousness patterns comprising sleep/wake patterns of the subject in response to the environment of the subject; and
    a container encasing the microcontroller, the volatile and non-volatile memory, the communications interface, the battery, the one or more electrical pads, the one or more actuating devices, and the at least one nozzle.

2. The patch of claim 1, further comprising a flexible circuit board with the microcontroller, the volatile and non-volatile memory, the communications interface, the battery, the one or more electrical pads, and the one or more actuating devices embedded thereon.

3. The patch of claim 1, wherein the one or more electrical pads are further configured to measure at least one of skin temperature and blood oxygen saturation levels of the subject.

4. The patch of claim 1, wherein the one or more electrical pads are further configured to sense pulse/blood oximetry and analyze sweat and other skin secretions of the subject.

5. The patch of claim 1, wherein the communications interface is configured to perform one or more of: communicate with other patches, transfer measured and calculated data to be stored at other patches containing memory, and trigger the delivery of stimuli in other patches that are capable of delivering such stimuli.

6. The patch of claim 5, wherein the communications interface is configured to communicate with the other patches by applying low power electrical signals to the skin of the subject such that the signals propagate on a surface of the skin to the other patches.

7. The patch of claim 1, wherein the container further comprises a vessel capable of storing various doses of the one or more agents to be delivered transdermally to the subject by the one or more actuating devices.

8. The patch of claim 1, further comprising photodiodes configured to measure environmental light exposure, and for estimating the total light dosage received by the subject over a period of time, wherein specific times relative to sleep onset/circadian phase at which the light stimuli were received can also be derived from these measurements.

9. The patch of claim 1, wherein the one or more agents are selected from the group consisting of one or more central nervous system depressants and one or more central nervous system stimulants.

10. A method of modulating the circadian phase of a subject in response to an environment of the subject, the method comprising:
    initializing a wearable skin-patch positioned on skin of the subject, the patch comprising a microcontroller, a volatile and non-volatile memory, a communications interface, a battery, one or more electrical pads, one or more actuating devices, and at least one nozzle;
    collecting and monitoring one or more of: polysomnographic data selected from the group consisting of brainwave data, eye movement data and muscle tone data, consciousness patterns, and actigraphy data, by the one or more electrical pads, of the subject;

estimating or determining, by the microcontroller, a circadian phase of the subject based on the collected and monitored activity/inactivity patterns and polysomnographic data; and delivery of one or more agents, through the at least one nozzle in controlled transdermal delivery, by the one or more actuating devices, to the skin of the subject based on the estimated or determined circadian phase;

wherein the delivery of the one or more agents is configured to modulate one or more of: the circadian phase and consciousness patterns comprising sleep/wake patterns of the subject in response to the environment of the subject.

11. The method of claim 10, wherein the one or more agents are selected from the group including one or more central nervous system depressants and one or more central nervous system stimulants.

* * * * *